(12) United States Patent
Mayes et al.

(10) Patent No.: US 7,781,576 B2
(45) Date of Patent: Aug. 24, 2010

(54) PROCESS FOR PREPARING A SYNTHETIC INTERMEDIATE FOR PREPARATION OF BRANCHED NUCLEOSIDES

(75) Inventors: Benjamin Alexander Mayes, Boston, MA (US); Adel Moussa, Burlington, MA (US)

(73) Assignee: Idenix Pharmaceuticals, Inc., Cambridge, MA (US)

( * ) Notice: Subject to any disclaimer, the term of this patent is extended or adjusted under 35 U.S.C. 154(b) by 824 days.

(21) Appl. No.: 11/644,304

(22) Filed: Dec. 22, 2006

(65) Prior Publication Data

US 2007/0203334 A1  Aug. 30, 2007

Related U.S. Application Data

(60) Provisional application No. 60/753,507, filed on Dec. 23, 2005.

(51) Int. Cl.
*C07H 19/48* (2006.01)
*C07H 19/22* (2006.01)
(52) U.S. Cl. ...................... 536/27.1; 536/28.1; 536/55.3
(58) Field of Classification Search ................ 536/27.1, 536/28.1, 55.3
See application file for complete search history.

(56) References Cited

U.S. PATENT DOCUMENTS

| | | | |
|---|---|---|---|
| 3,074,929 A | 1/1963 | Hitchings et al. |
| 3,116,282 A | 12/1963 | Hunter |
| 3,480,613 A | 11/1969 | Walton |
| 3,798,209 A | 3/1974 | Wilkowski et al. |
| 3,891,623 A | 6/1975 | Vorbruggen et al. |
| 4,022,889 A | 5/1977 | Bannister et al. |
| 4,058,602 A | 11/1977 | Beisler et al. |
| RE29,835 E | 11/1978 | Wilkowski et al. |
| 4,209,613 A | 6/1980 | Vorbruggen et al. |
| 4,239,753 A | 12/1980 | Skulnick et al. |
| 4,294,766 A | 10/1981 | Schmidt et al. |
| 4,522,811 A | 6/1985 | Eppstein et al. |
| 4,605,659 A | 8/1986 | Verheyden et al. |
| 4,689,404 A | 8/1987 | Kawada et al. |
| 4,754,026 A | 6/1988 | Kawada et al. |
| 4,814,477 A | 3/1989 | Wijnberg et al. |
| 4,880,784 A | 11/1989 | Robins et al. |
| 4,952,740 A | 8/1990 | Juge et al. |
| 4,957,924 A | 9/1990 | Beuchamp |
| 5,034,394 A | 7/1991 | Daluge |
| 5,122,517 A | 6/1992 | Vince et al. |
| 5,149,794 A | 9/1992 | Yatvin et al. |
| 5,157,027 A | 10/1992 | Biller |
| 5,194,654 A | 3/1993 | Hostetler et al. |
| 5,200,514 A | 4/1993 | Chu |
| 5,223,263 A | 6/1993 | Hostetler et al. |
| 5,246,924 A | 9/1993 | Fox et al. |
| 5,256,641 A | 10/1993 | Yatvin et al. |
| 5,256,797 A | 10/1993 | Chou et al. |
| 5,322,955 A | 6/1994 | Matsumoto et al. |
| 5,371,210 A | 12/1994 | Chou et al. |
| 5,372,808 A | 12/1994 | Blatt et al. |
| 5,391,769 A | 2/1995 | Matsumoto et al. |
| 5,401,861 A | 3/1995 | Chou et al. |
| 5,411,947 A | 5/1995 | Hostetler et al. |
| 5,463,092 A | 10/1995 | Hostetler et al. |
| 5,539,116 A | 7/1996 | Liotta et al. |
| 5,543,389 A | 8/1996 | Yatvin et al. |
| 5,543,390 A | 8/1996 | Yatvin et al. |
| 5,543,391 A | 8/1996 | Yatvin et al. |
| 5,554,728 A | 9/1996 | Basava et al. |
| 5,565,438 A | 10/1996 | Chu et al. |
| 5,567,688 A | 10/1996 | Chu et al. |
| 5,587,362 A | 12/1996 | Chu et al. |
| 5,606,048 A | 2/1997 | Chou et al. |
| 5,676,942 A | 10/1997 | Testa et al. |
| 5,696,277 A | 12/1997 | Hostetler et al. |
| 5,738,845 A | 4/1998 | Imakawa |
| 5,744,600 A | 4/1998 | Mansuri et al. |
| 5,750,676 A | 5/1998 | Vorbruggen et al. |
| 5,763,418 A | 6/1998 | Matsuda et al. |
| 5,780,617 A | 7/1998 | Van den Bosch et al. |
| 5,789,608 A | 8/1998 | Glazier |
| 5,821,357 A | 10/1998 | Chou et al. |

(Continued)

FOREIGN PATENT DOCUMENTS

CA          2252144          4/2000

(Continued)

OTHER PUBLICATIONS

U.S. Appl. No. 10/845,976, filed May 14, 2004, Storer, et al.

(Continued)

*Primary Examiner*—Shaojia Anna Jiang
*Assistant Examiner*—Ganapathy Krishnan
(74) *Attorney, Agent, or Firm*—Jones Day

(57) ABSTRACT

A process is provided for the preparation of a key intermediate in the preparation of 2'-branched nucleoside compounds. The process includes contacting a protected precursor 3,4-O-isopropylidene-2-C-substituted-D-arabinono-1,5-lactone with a fluorinating agent under anhydrous conditions and converting the precursor into a protected 2-deoxy-2-halo-2-C-disubstituted ribono-1,5-lactone and optionally into a 2-deoxy-2-halo-2-C-disubstituted ribono-1,4-lactone.

38 Claims, No Drawings

U.S. PATENT DOCUMENTS

| | | | |
|---|---|---|---|
| 5,830,455 A | 11/1998 | Valtuena et al. |
| 5,849,696 A | 12/1998 | Chretien et al. |
| 5,908,621 A | 6/1999 | Glue et al. |
| 5,928,636 A | 7/1999 | Alber et al. |
| 5,942,223 A | 8/1999 | Bazer et al. |
| 5,977,061 A | 11/1999 | Holy et al. |
| 5,977,325 A | 11/1999 | McCarthy et al. |
| 5,980,884 A | 11/1999 | Blatt et al. |
| 6,002,029 A | 12/1999 | Hostetler et al. |
| 6,063,628 A | 5/2000 | Loeb et al. |
| 6,140,310 A | 10/2000 | Glazier |
| 6,153,594 A | 11/2000 | Borretzen et al. |
| 6,156,501 A | 12/2000 | McGall et al. |
| 6,172,046 B1 | 1/2001 | Albrecht |
| 6,248,878 B1 | 6/2001 | Matulic-Adamic et al. |
| 6,252,060 B1 | 6/2001 | Hostetler |
| 6,271,212 B1 | 8/2001 | Chu et al. |
| 6,277,830 B1 | 8/2001 | Ganguly et al. |
| 6,312,662 B1 | 11/2001 | Erion et al. |
| 6,340,690 B1 | 1/2002 | Bachand et al. |
| 6,348,587 B1 | 2/2002 | Schinazi et al. |
| 6,369,040 B1 | 4/2002 | Acevedo et al. |
| 6,395,716 B1 | 5/2002 | Gosselin et al. |
| 6,436,437 B1 | 8/2002 | Yatvin et al. |
| 6,444,652 B1 | 9/2002 | Gosselin et al. |
| 6,448,392 B1 | 9/2002 | Hostetler et al. |
| 6,455,508 B1 | 9/2002 | Ramasamy et al. |
| 6,458,772 B1 | 10/2002 | Zhou et al. |
| 6,458,773 B1 | 10/2002 | Gosselin et al. |
| 6,472,373 B1 | 10/2002 | Albrecht |
| 6,495,677 B1 | 12/2002 | Ramasamy et al. |
| 6,566,344 B1 | 5/2003 | Gosselin et al. |
| 6,566,365 B1 | 5/2003 | Storer |
| 6,569,837 B1 | 5/2003 | Gosselin et al. |
| 6,573,248 B2 | 6/2003 | Ramasamy et al. |
| 6,596,700 B2 | 7/2003 | Sommadossi et al. |
| 6,599,887 B2 | 7/2003 | Hostetler et al. |
| 6,605,614 B2 | 8/2003 | Bachand et al. |
| 6,642,206 B2 | 11/2003 | Ramasamy et al. |
| 6,660,721 B2 | 12/2003 | Devos et al. |
| 6,748,161 B2 | 6/2004 | Ko et al. |
| 6,752,981 B1 | 6/2004 | Erion et al. |
| 6,777,395 B2 | 8/2004 | Bhat et al. |
| 6,784,161 B2 | 8/2004 | Ismaili et al. |
| 6,784,166 B2 | 8/2004 | Devos et al. |
| 6,787,526 B1 | 9/2004 | Bryant et al. |
| 6,812,219 B2 | 11/2004 | LaColla et al. |
| 6,815,542 B2 | 11/2004 | Hong et al. |
| 6,831,069 B2 | 12/2004 | Tam et al. |
| 6,833,361 B2 | 12/2004 | Hong et al. |
| 6,846,810 B2 | 1/2005 | Martin et al. |
| 6,875,751 B2 | 4/2005 | Imbach et al. |
| 6,908,924 B2 | 6/2005 | Watanabe et al. |
| 6,911,424 B2 | 6/2005 | Schinazi et al. |
| 6,914,054 B2 | 7/2005 | Sommadossi et al. |
| 6,927,291 B2 | 8/2005 | Jin et al. |
| 6,946,115 B2 | 9/2005 | Erion et al. |
| 6,946,450 B2 | 9/2005 | Gosselin et al. |
| 6,949,522 B2 | 9/2005 | Otto et al. |
| 6,965,033 B2 | 11/2005 | Jiang et al. |
| 7,056,895 B2 | 6/2006 | Ramasamy et al. |
| 7,094,770 B2 | 8/2006 | Watanabe et al. |
| 7,101,861 B2 | 9/2006 | Sommadossi et al. |
| 7,105,493 B2 | 9/2006 | Sommadossi et al. |
| 7,105,499 B2 | 9/2006 | Carroll et al. |
| 7,125,855 B2 | 10/2006 | Bhat et al. |
| 7,144,868 B2 | 12/2006 | Roberts et al. |
| 7,148,206 B2 | 12/2006 | Sommadossi et al. |
| 7,151,089 B2 | 12/2006 | Roberts et al. |
| 7,157,434 B2 | 1/2007 | Keicher et al. |
| 7,157,441 B2 | 1/2007 | Sommadossi et al. |
| 7,163,929 B2 | 1/2007 | Sommadossi et al. |
| 7,169,766 B2 | 1/2007 | Sommadossi et al. |
| 7,202,224 B2 | 4/2007 | Eldrup et al. |
| 2002/0019363 A1 | 2/2002 | Ismaili et al. |
| 2002/0035085 A1 | 3/2002 | Sommadossi et al. |
| 2002/0052345 A1 | 5/2002 | Erion et al. |
| 2002/0055473 A1 | 5/2002 | Ganguly et al. |
| 2002/0055483 A1 | 5/2002 | Watanabe et al. |
| 2002/0095033 A1 | 7/2002 | Ramasamy et al. |
| 2002/0099072 A1 | 7/2002 | Bachand et al. |
| 2002/0127203 A1 | 9/2002 | Albrecht |
| 2002/0147160 A1 | 10/2002 | Bhat et al. |
| 2002/0156030 A1 | 10/2002 | Ramasamy et al. |
| 2002/0173490 A1 | 11/2002 | Jiang et al. |
| 2002/0198171 A1 | 12/2002 | Schinazi et al. |
| 2003/0008841 A1 | 1/2003 | Devos et al. |
| 2003/0028013 A1 | 2/2003 | Hong et al. |
| 2003/0039630 A1 | 2/2003 | Albrecht |
| 2003/0050229 A1 | 3/2003 | Sommadossi et al. |
| 2003/0053986 A1 | 3/2003 | Zahm |
| 2003/0055013 A1 | 3/2003 | Brass |
| 2003/0060400 A1 | 3/2003 | LaColla et al. |
| 2003/0083306 A1 | 5/2003 | Imbach et al. |
| 2003/0083307 A1 | 5/2003 | Devos et al. |
| 2003/0087873 A1 | 5/2003 | Stuyver et al. |
| 2003/0124512 A1 | 7/2003 | Styuver |
| 2003/0220290 A1 | 11/2003 | Gosselin et al. |
| 2003/0225028 A1 | 12/2003 | Gosselin et al. |
| 2003/0225029 A1 | 12/2003 | Stuyver |
| 2003/0225037 A1 | 12/2003 | Storer et al. |
| 2003/0236216 A1 | 12/2003 | Devos et al. |
| 2004/0002476 A1 | 1/2004 | Stuyver et al. |
| 2004/0002596 A1 | 1/2004 | Hong et al. |
| 2004/0006002 A1 | 1/2004 | Sommadossi et al. |
| 2004/0023921 A1 | 2/2004 | Hong et al. |
| 2004/0059104 A1 | 3/2004 | Cook et al. |
| 2004/0063622 A1 | 4/2004 | Sommadossi et al. |
| 2004/0063658 A1 | 4/2004 | Roberts et al. |
| 2004/0067901 A1 | 4/2004 | Bhat et al. |
| 2004/0072788 A1 | 4/2004 | Bhat et al. |
| 2004/0077587 A1 | 4/2004 | Sommadossi et al. |
| 2004/0097461 A1 | 5/2004 | Sommadossi et al. |
| 2004/0097462 A1 | 5/2004 | Sommadossi et al. |
| 2004/0101535 A1 | 5/2004 | Sommadossi et al. |
| 2004/0102414 A1 | 5/2004 | Sommadossi et al. |
| 2004/0110717 A1 | 6/2004 | Carroll et al. |
| 2004/0110718 A1 | 6/2004 | Devos et al. |
| 2004/0121980 A1 | 6/2004 | Martin et al. |
| 2004/0147464 A1 | 7/2004 | Roberts et al. |
| 2004/0229839 A1 | 11/2004 | Babu et al. |
| 2004/0248844 A1 | 12/2004 | Ismaili et al. |
| 2004/0259934 A1 | 12/2004 | Olsen et al. |
| 2004/0266722 A1 | 12/2004 | Devos et al. |
| 2004/0266723 A1 | 12/2004 | Otto et al. |
| 2004/0266996 A1 | 12/2004 | Rabi |
| 2005/0009737 A1 | 1/2005 | Clark et al. |
| 2005/0020825 A1 | 1/2005 | Storer et al. |
| 2005/0031588 A1 | 2/2005 | Sommadossi et al. |
| 2005/0038240 A1 | 2/2005 | Connolly et al. |
| 2005/0090463 A1 | 4/2005 | Roberts et al. |
| 2005/0101550 A1 | 5/2005 | Roberts et al. |
| 2005/0107312 A1 | 5/2005 | Keicher et al. |
| 2005/0113330 A1 | 5/2005 | Imbach et al. |
| 2005/0119200 A1 | 6/2005 | Roberts et al. |
| 2005/0124532 A1 | 6/2005 | Sommadossi et al. |
| 2005/0137141 A1 | 6/2005 | Hilfinger et al. |
| 2005/0137161 A1 | 6/2005 | Sommadossi et al. |
| 2005/0215511 A1 | 9/2005 | Roberts et al. |
| 2006/0040890 A1 | 2/2006 | Martin et al. |
| 2006/0111311 A1 | 5/2006 | Keicher et al. |
| 2006/0166865 A1 | 7/2006 | Sommadossi et al. |
| 2006/0194835 A1 | 8/2006 | Dugourd et al. |
| 2006/0199783 A1 | 9/2006 | Wang et al. |

| | | | | | | |
|---|---|---|---|---|---|---|
| 2006/0241064 | A1 | 10/2006 | Roberts et al. | WO | WO 01/79246 | 4/2001 |
| 2007/0015905 | A1 | 1/2007 | LaColla et al. | WO | WO 01/32153 | 5/2001 |
| 2007/0060503 | A1 | 3/2007 | Gosselin et al. | WO | WO 01/92282 | 6/2001 |
| 2007/0060504 | A1 | 3/2007 | Gosselin et al. | WO | WO 01/47935 | 7/2001 |
| 2007/0203334 | A1 | 8/2007 | Mayes et al. | WO | WO 01/49700 | 7/2001 |

FOREIGN PATENT DOCUMENTS

| | | | | | |
|---|---|---|---|---|---|
| DE | 1919307 | 1/1971 | WO | WO 01/60315 | 8/2001 |
| DE | 2122991 | 11/1972 | WO | WO 01/68663 | 9/2001 |
| DE | 2508312 | 9/1976 | WO | WO 01/90121 | 11/2001 |
| DE | 140254 | 2/1980 | WO | WO 01/91737 | 12/2001 |
| DE | 3512781 | 10/1985 | WO | WO 01/96353 | 12/2001 |
| DE | 4224737 | 2/1994 | WO | WO 02/03997 | 1/2002 |
| DE | 102005012681 | 9/2006 | WO | WO 02/18404 | 3/2002 |
| EP | 0288847 | 4/1988 | WO | WO 02/32414 | 4/2002 |
| EP | 0180276 | 12/1988 | WO | WO 02/32920 | 4/2002 |
| EP | 0352248 | 1/1990 | WO | WO 02/48165 | 6/2002 |
| EP | 0494119 | 1/1992 | WO | WO 02/057287 | 7/2002 |
| EP | 0526655 | 2/1993 | WO | WO 02/057425 | 7/2002 |
| EP | 0553358 | 8/1993 | WO | WO 02/070533 | 9/2002 |
| EP | 0587364 | 3/1994 | WO | WO 02/094289 | 11/2002 |
| EP | 0742287 | 11/1996 | WO | WO 02/100415 | 12/2002 |
| EP | 0747389 | 12/1996 | WO | WO 03/024461 | 3/2003 |
| EP | 0350287 | 9/2000 | WO | WO 03/026589 | 4/2003 |
| EP | 0650371 | 11/2000 | WO | WO 03/026675 | 4/2003 |
| FR | 1521076 | 4/1968 | WO | WO 03/039523 | 5/2003 |
| FR | 1581628 | 9/1969 | WO | WO 03/051899 | 6/2003 |
| FR | 2662165 | 11/1991 | WO | WO 03/081899 | 6/2003 |
| GB | 924246 | 4/1963 | WO | WO 03/061385 | 7/2003 |
| GB | 984877 | 3/1965 | WO | WO 03/061576 | 7/2003 |
| GB | 1187824 | 5/1966 | WO | WO 03/062255 | 7/2003 |
| GB | 1163102 | 9/1969 | WO | WO 03/062256 | 7/2003 |
| GB | 1163103 | 9/1969 | WO | WO 03/062257 | 7/2003 |
| GB | 1209654 | 10/1970 | WO | WO 03/063771 | 8/2003 |
| GB | 1542442 | 3/1979 | WO | WO 03/068162 | 8/2003 |
| JP | 71021872 | 3/1968 | WO | WO 03/068164 | 8/2003 |
| JP | 48048495 | 9/1971 | WO | WO 03/068244 | 8/2003 |
| JP | 61212592 | 9/1986 | WO | WO 03/072757 | 9/2003 |
| JP | 61263995 | 11/1986 | WO | WO 03/093290 | 11/2003 |
| JP | 61263996 | 11/1986 | WO | WO 03/099840 | 12/2003 |
| JP | 63215694 | 9/1988 | WO | WO 03/100017 | 12/2003 |
| JP | 02091022 | 3/1990 | WO | WO 03/105770 | 12/2003 |
| JP | 06135988 | 5/1994 | WO | WO 03/106577 | 12/2003 |
| JP | 06211890 | 8/1994 | WO | WO 2004/000858 | 12/2003 |
| JP | 06228186 | 8/1994 | WO | WO 2004/002422 | 1/2004 |
| JP | 06293645 | 10/1994 | WO | WO 2004/002999 | 1/2004 |
| JP | 09059292 | 3/1997 | WO | WO 2004/003000 | 1/2004 |
| WO | WO 89/02733 | 4/1989 | WO | WO 2004/003138 | 1/2004 |
| WO | WO 90/00555 | 1/1990 | WO | WO 2004/007512 | 1/2004 |
| WO | WO 91/16920 | 11/1991 | WO | WO 2004/009020 | 1/2004 |
| WO | WO 91/18914 | 12/1991 | WO | WO 2004/023921 | 3/2004 |
| WO | WO 91/19721 | 12/1991 | WO | WO 2004/028481 | 4/2004 |
| WO | WO 92/15308 | 9/1992 | WO | WO 2004/041203 | 5/2004 |
| WO | WO 92/18517 | 10/1992 | WO | WO 2004/043977 | 5/2004 |
| WO | WO 93/00910 | 1/1993 | WO | WO 2004/043978 | 5/2004 |
| WO | WO 94/01117 | 1/1994 | WO | WO 2004/044132 | 5/2004 |
| WO | WO 94/26273 | 11/1994 | WO | WO 2004/046159 | 6/2004 |
| WO | WO 96/15132 | 5/1996 | WO | WO 2004/046331 | 6/2004 |
| WO | WO 98/16184 | 4/1998 | WO | WO 2004/052899 | 6/2004 |
| WO | WO 99/15194 | 4/1999 | WO | WO 2004/058792 | 7/2004 |
| WO | WO 99/23104 | 5/1999 | WO | WO 2004/065398 | 8/2004 |
| WO | WO 99/43691 | 9/1999 | WO | WO 2004/072090 | 8/2004 |
| WO | WO 99/45016 | 9/1999 | WO | WO 2004/080466 | 9/2004 |
| WO | WO 99/52514 | 10/1999 | WO | WO 2004/084796 | 10/2004 |
| WO | WO 99/59621 | 11/1999 | WO | WO 2004/096149 | 11/2004 |
| WO | WO 99/64016 | 12/1999 | WO | WO 2004/106356 | 12/2004 |
| WO | WO 00/09531 | 2/2000 | WO | WO 2005/003147 | 1/2005 |
| WO | WO 00/25799 | 5/2000 | WO | WO 2005/012327 | 2/2005 |
| WO | WO 00/37110 | 6/2000 | WO | WO 2005/020884 | 3/2005 |
| WO | WO 00/52015 | 9/2000 | WO | WO 2005/020885 | 3/2005 |
| WO | WO 01/81359 | 11/2000 | WO | WO 2005/021568 | 3/2005 |
| WO | WO 01/18013 | 3/2001 | WO | WO 2005/030258 | 4/2005 |
| | | | WO | WO 2005/042556 | 5/2005 |
| | | | WO | WO 2005/123087 | 12/2005 |
| | | | WO | WO 2006/002231 | 1/2006 |

| WO | WO 2006/012078 | 2/2006 |
| WO | WO 2006/012440 | 2/2006 |
| WO | WO 2006/016930 | 2/2006 |
| WO | WO 2006/031725 | * 3/2006 |
| WO | WO 2006/037028 | 4/2006 |
| WO | WO 2006/037227 | 4/2006 |
| WO | WO 2006/063717 | 6/2006 |
| WO | WO 2006/065335 | 6/2006 |
| WO | WO 2006/097323 | 9/2006 |
| WO | WO 2006/100087 | 9/2006 |
| WO | WO 2006/121820 | 11/2006 |
| WO | WO 2006/130532 | 12/2006 |
| WO | WO 2007/011777 | 1/2007 |
| WO | WO 2007/025304 | 1/2007 |

OTHER PUBLICATIONS

U.S. Appl. No. 11/005,443, filed Dec. 6, 2004, Gosselin, et al.
U.S. Appl. No. 11/516,928, filed Sep. 6, 2006, Sommadossi, et al.
U.S. Appl. No. 11/644,304, filed Dec. 22, 2006, Mayes, et al.
Afdhal, et al., Enhanced antiviral efficacy for valopicitabine glue PEG-interferon in hepatitis C patients with HCV genotype-1 infection. Journal of Hepatology 2005, vol. 42, Supplement 2, p. 39-40.
Alt, et al., "Specific inhibition of hepatitis C viral gene expression by antisense phosphorothioate oligodeoxynucleotides," Hepatology, 22:707-717 (1995).
Alt, et al., "Core Specific Antisense Phosphorothioate Oligodeoxynucleotides as Ptent and Specific Inhibitors of Hepatitis C Viral Translation." Arch. Virol. (1997) 142: 589-599.
Altmann, et al., "The Synthesis of 1'-Methyl Carbocyclic Thymidine and Its Effect on Nucleic Acid Duplex Stability," Synlett, Thieme Verlag. Stuttgart, De, 10:853-855 (1994).
Altmann, et al., The Effects of 2'- and 3'-Alkyl Substituents on Oligonucleotide Hybridization and Stability, Biorganic & Medicinal Chemistry Letter. 1994. 4. No. 16. 1969-74.
Awano, et al., "Nucleosides and Nucleotides, Part 144 Synthesis and Antiviral Activity of 5-Substituted (2's)-2'-Deoxy-2'-C-Methylycytidines and -Urdines," Archiv Der Pharmazie, VCH Verlagsgesellschaft Mbh, Weinheim, DE, vol. 329, Feb. 1, 1996, pp. 66-72.
Baginsky, S.G., et al., "Mechanism of Action of a Pestivirus Antiviral Compound," PNAS USA 2000 97(14), 7981-7986.
Battaglia, A.M. et al., "Comibination Therapy with Interferon and Ribavirin in the Treatment of Chronic Hepatitis C. Infection", Ann Pharmacother, 34:487-494 (2000).
Beigelman et al., "New synthesis of 2'-C-methylnucleosides starting from D-glucose and D-ribose" Carbohydrate Res., 1987,1166,.219-232.
Beigelman et al., "A general method for synthesis of 3'—alkylnucleosides," Nucleic Acids Symp. Ser., vol. 9, 1981, pp. 115-118.
Beigelman et al., "Epimerization During the Acetolysis of 3-O-Acetyl-5-O-Benzoyl-1,2-o-Isopropylidene-3-C-Methyl-a, D-Ribofuranose. Synthesis of 3'-C-Methylnucleosides with the B-D-ribo-and a-D-arabino Configurations," Carbohydrate Research, 181:77-88 (1988).
Beigelman et al., Functionally complete analogs of nucleosides. The use of D-gluclose for the synthesis of 2-C-methyl-D-ribose derivatives and related nucleosides. Biorrganicheskaya Khimiya. 1986, vol. 12(10), pp. 1359-1365.
Berenguer, M., et al., "Hepatitis B and C viruses: Molecular identification and targeted antiviral therapies," Proceedings of the Association of American Physicians, 110(2), 98-112 (1998).
Berenguer, M., et al., "Hepatitis C virus in the transplnat setting", Antivir. Ther., 3 (Suppl 3):125-136 (1998).
Berman, E., et al., "Synergistic Cytotoxic Effect of Azidothymidine and Recombinant Interferon Alpha on Normal Human Bone Marrow Progenitor Cells," Blood, 74(4):1281-1286 (1989).
Bhat et al. (Oral Session V, Hepatitis C Virus, Flaviviridae, 2003 (Oral Session V, Hepatitis C Virus, Flaviviridae; 16th International Conference on Antiviral Research (Apr. 27, 2003, Savannah, GA); p. A75).
Bhopale, Girish Mahadeorao, et al., "Emerging drugs for chronic hepatitis C," Hepatology Research (2005), 32(3), 146-153.

Bianco A., et al. "Synthesis of a New Carbocyclic Nucleoside Analog", Tetrahedron Letters, 38(36):6433-6436, 1997.
Billich, et al., "Nucleoside Phosphotransferase from Malt Sprouts." Biol. Chem. Hoppe-Seyler, vol. 367, pp. 267-278, Apr. 1986.
Bio, et al., "Practical Synthesis of a Potent Hepatitis C Virus RNA Replication Inhibitor." Journal of Organic Chemistry (2004), 69(19), 6257-6266.
Bloch A., et al., "The Role of the 5'-Hydroxyl Group of Adenosine in Determining Substrate Specificity for Adenosine Deaminase," J. Med. Chem., 10(5):908-12 (Sep. 1967).
Browne, M.J., et al., "2',3'-didehydro-3'-deoxythymidine (d4T) in patients with AIDS or AIDS-Related Complex: A Phase I Trial," J. Infect. Dis., 167(1):21-29 (1993).
Bryant M.L., et al., "Antiviral L-Nucleosides Specific for Hepatitis B Virus Infection," Antimicrobial Agents and Chemotherapy, 45(1):229-235 (Jan. 2001).
Cappelacci, et al. "Synthesis, Biological Evaluation, and Molecular Modeling of Ribose-Modified Adenosine Analogues as Adenosine Receptor Agonists." Journal of Medicinal Chemistry (2005), 48(5), 1550-1562.
Cappelacci, et al. "Ribose-modified nucleosides as ligands for adenosine receptors: Synthesis, conformational analysis, and biological evaluation of 1'—C-methyl denosine analogues," J. Med. Chem., vol. 45, 2002, pp. 1196-1202.
Carroll, S.S., "Nucleoside analog inhibitors of hepatitis C virus replication," Infectious Disorders: Drug Targets (2006), 6(1), 17-29.
Carroll S.S., et al., "Inhibition of hepatitis C virus RNA replication by 2'-modified nucleoside analogs," J. Biol. Chem., 278(14): 11979-11984 (2003).
Cavelier, F., et al., "Studies of Selective Boc Removal in the Presence of Silyl Ethers," Tetrahedron Letters, 37: 5131-5134 (1996).
Chand, Pooran; et al., "Synthesis of (2S,3S,4R,5R)-2-(4-amino-5H-pyrrolo[3,2-d]pyrimidin-7-yl)-5-(hydroxymethyl)-3-methylpyrrolidine-3,4-diol, an analog of potent HCV inhibitor." Collection Symposium Series (2005), 7(Chemistry of Nucleic Acid Components), 329-332.
Chen et al., Heterocycles, vol. 28, No. 2, 1989, pp. 593-601.
Chiacchio, et al., "Stereoselective synthesis of 2'-amino-2',3'-dideoxynucleosides by nitrone 1,3-dipolar cycloaddition: A new efficient entry toward d4T and its 2-methyl analougue," J. Org. Chem, vol. 64, 1999, pp. 28-36.
Chiaramonte, et al., "Inhibition of CMP-Sialic Acid Transport into Golgi Vesicles by Nucleoside Monophates." Biochemistry 2001, 40, 14260-14267.
Clark, et al., Synthesis and antiviral activity . . . , Bioorganic & Medicinal Chemistry Letters, 16, 2006, 1712-1715.
Clark, et al., "Design, Synthesis, and Antiviral Activity of 2'-Deoxy-2'-fluoro-2'-C-methylcytidine, a Potent Inhibitor of Hepatitis C Virus Replication." Journal of Medicinal Chemistry (2005), 48(17), 5504-5508.
Coelmont, Lotte, "Ribavirin antagonizes the in vitro anti-hepatitis C virus activity of 2'-C-methycytidine, the active component of valopicitabine," Antimicrobial Agents and Chemotherapy (2006), 50(10), 3444-3446.
Colacino, J. M., "Review article: Mechanisms for the anti-hepatitis B virus activity and mitochondreal toxiciety of fialurdine (FIAU)," Antivirul Res., 29(2-3): 125-39 (1996).
Cook, G.S., "Improving the treatment of hepatitis C infection in the UK," Expert Opinion on Pharmacotherapy, (2007) vol. 8, No. 2, pp. 183-191.
Cornberg, M., et al., "Present and future therapy for hepatitis C virus," Expert review of Anti-Infective Therapy, (2006) vol. 4, No. 5, pp. 781-793.
Cretton-Scott, E., et al., "Pharmacokinetics of B-L-2'-Deoxyctidine Prodrugs in Monkeys," Antiviral res., 50:A44 (2001).
Cui, L., et al., "Cellular and molecular events leading to mitochondrial toxicity of 1-(2-deoxy-2-fluoro-1-β-D-arabinofuranosyl)5-iodouracil in human liver cells," J. Clin. Invest., 95:555-563 (1995).
Czernecki, S., et al., "Synthesis of various 3'-branched 2', 3'-unsaturated pyrimidine nucleosides as potential anti-HIV agents," J. Org. Chem., 57: 7325-7328 (1992).

Czernecki, S., et al., "Synthesis of 2'-deoxy-2'-spirocyclopropyl cytidine as potential inhibitor of ribonucleotide diphosphate reductase," Can. J. Chem., vol. 71, 1993, pp. 413-416.

Dalpiaz, et al., "Temperature dependence of the affinity enhancement of selective adenosine A1 receptor agonism: a thermodynamic analysis." European Journal of Pharmacology (2002), 448(2-3), 123-131.

Daniels et al., "Tautomerism of Uracil and Thymine in Aqueous Solution: Spectroscopic Evidence", Proc. Nat. Acad. Sci. USA, vol. 69, No. 9, pp. 2488-2491, 1972.

Davis, G.L., "Current therapy for chronic Hepatitis C," *Gastroenterology* 118:S104-S114 (2000).

Davis, G.L., "New Therapies: Oral Inhibitors and Immune Modulators," Clinics in Liver Disease, (2006) vol. 10, No. 4, pp. 867-880.

Davisson, V.J., et al., "Synthesis of Nucleotide 5'-Diphosphates from 5'-O-Tosyl Nucleosides," J. Org. Chem., 52(9):1794-1801 (1987).

De Francesco, et al. "Approaching a new era for hepatitis C virus therapy: Inhibitors of the NS3-4A serine protease and the NS5B RNA-dependent RNA polymerase." Antiviral Research, 58: 1-16 (2003).

De Lombaert, S., et al., "N-Phosphonomethyl dipeptides and their phosphonate prodrugs, a new generation of neutral endopeptidase (NEP, EC 3.4.24.11) inhibitors," *J. Med. Chem.*, 37:498-511 (1994).

Ding, et al., "Synthesis of 2'-b-C-methyl toyocamycin and sangivamycin analogs as potential HCV inhibitors." Bioorganic & Medicinal Chemistry Letters (2005), 15(3), 725-727.

Ding, et al., "Synthesis of 9-(2-b-C-methyl-b-D-ribofuranosyl)-6-substituted purine derivatives as inhibitors of HCV RNA replication." Bioorganic & Medicinal Chemistry Letters (2005), 15(3), 709-713.

Dornsife, R.E., et al, "In vitro potency of inhibition by antiviral drugs of hematopoietic progenitor colony formation correlates with exposure at hemotoxic levels in Human Immunodefciency Virus-positive humans," *Anrimicrob. Agents Chemother.*, 40(2):514-519 (1996).

Dutartre, H., et al., "General catalytic deficiency of hepatitis C virus RNA polymerase with an S282T mutation and mutually exclusive resistance towards 2'-modified nucleotide analogues," Antimicrobial Agents and Chemotherapy, (2006) vol. 50, No. 12, pp. 4161-4169.

Dymock, B.W., et al., "Review: Novel approaches to the treatment of hepatitis C virus infection," *Antiviral Chemistry & Chemotherapy*, 11(2):79-95 (2000).

Eldrup et al., "Structure-Activity Relationship of Heterobase-Modified 2'-C-Methyl Ribonucleosides as Inhibitors of Hepatitis C Virus RNA Replication." Department of Medicinal Chemistry, Isis Pharmaceuticals, Carlsbad, CA, USA. Journal of Medicinal Chemistry (2004), 47(21), 5284-5297.

Eldrup, et al., "Structure-Activity Relationship of Purine Ribonucleosides for Inhibition of Hepatitis C Virus RNA-Dependent RNA Polymerase.", Department of Medicinal Chemistry, Isis Pharmaceuticals, Carlsbad, CA, USA. Journal of Medicinal Chemistry (2004), 47(9), 2283-2295.

Eldrup, et al., Oral Session V, Hepatitis C Virus, Flaviviridae; 16th International Conference on Antiviral Research (Apr. 27, 2003, Savannah, Ga.) p. A75-77.

Faivre-Buet, et al., "Synthesis of 1'-Deoxypsicofuanosyl-Dexoynucleosides as Potential Anti-HIV Agents." Nucleosides & Nucleotides, vol. 11, No. 7, 1992, pp. 1411-1424.

Farkus, J., et al., "Nucleic acid components and their analogues. LXXIX. Synthesis of methyl 1-deoxy-D-psicofuranosides substituted at C(1) with halo atoms or mercapto group," Collection Czechoslov. Chem. Comm., vol. 31, 1966, pp. 1535-1543.

Farkas, J., et al., "Nucleic acids components and their analogues. XCIV. Synthesis of 6-amino0-(1-deoxy-beta-D-psicofuranosyl)purine" Collection Czechoslov. Chem. Comm., vol. 32, 1967, pp. 2663-2667.

Farquhar et al., "Biologically reversible phosphate-protective groups," *J. Phurm. Sci.*, 1983, 72(3): 324.

Farquhar, D., et al., "Synthesis and biological evaluation of 9-[5'-(2-oxo-1,3,2-oxazaphosphorinan-2-yl)-β-D-arabinosyl]adenine and 9-[5'-(2-oxo-1,3,2-dioxazaphosphorinan-2-yl)-β-D-arabinosyl]adenine: Potential neutral precursors of 9-[β-D-arabinofuranosyl]adenine 5'-monophosphate," *J. Med. Chem.* 28:1358-1381 (1985).

Farquhar, D., et al., "Synthesis and biological evaluation of neutral derivatives of 3-fluoro-2'-deoxyuridine 5'-phosphate," J. Med Chem. 26: (1983); 1153-1158.

Feast, A.A.J., et al., "Studies on the D-Glucosaccharinic Acids," Acta Chemica Scandinavica 19(5):1127-1134 (1965).

Federov, et al., "3'—C-Branched 2'—deoxy-5-methyluridines: Synthesis, enzyme inhibition, and antiviral properties," J. Med. Chem., vol. 35, 1992, pp. 4567-4575.

Ferrari R,, et al., "Characterization of soluble hepatitis C virus RNA-dependent RNA polymerase expressed in *Escherichia coli*," *Journal of Virology*, 73(2), 1649-1654 (1999).

Fischl, M.A., et al., "Zalcitabine compared with zidovudine in patients with advanced HIV-1 infection who received previous zidovudine therapy," *Ann. Intern. Med.*, 18(10):762-769 (1993).

Fox, J. J., et al., "Thiolation of nucleosides. II. Synthesis of 5-methyl-2'-deoxycytidine and related pyrimidine nucleosides," J. Am. Chem. Soc., 81: 178-187 (Jan. 5, 1959).

Francesco, et al. Antiviral Research 58 (2003) 1-16.

Franchetti, et al., "2'—C-Methyl analogues of selective adenosine receptor agonists: Synthesis and binding studies," J. Med. Chem., vol. 41(10), 1998, pp. 1708-1715.

Franchetti, et al., "Antitumor Activity of C-Methyl-b-D-ribofuranosyladenine Nucleoside Ribonucleotide Reductase Inhibitors." Journal of Medicinal Chemistry (2005), 48(15), 4983-4989.

Freed, J.J., et al., "Evidence for acyloxymethyl esters of pyrimidine 5'-deoxyribonucleotides as extracellular sources of ative 5'-deoxyribonucleotides in cultured cells," *Biochemical Pharmacology*. 38:3193-3198 (1989).

Fujimori, et al., "A Convenient and Stereoselective Synthesis of 2'-Deoxy-[beta]-L-nucleosides," Nucleosides & Nucleotides, 11(2-4), 341-349 (1992); only CAPLUS abstract supplied.

Furukawa, Y., et al. "A novel method for synthesis of purine nucleosides using Friedel-Crafts catalysts," Chem. Pharm. Bull., 16(6):1076-1080 (Jun. 1968).

Galderisi, U., et al., "Antisense oligonucleoties as therapeutic agents," Journal of Cellular Physiology, 181(2):251-257 (Nov. 1999).

Gallo, et al., "2'-C-Methyluridine Phosphoramidite: A New Building Block for the Preparation of RNA Analogues Carrying the 2'-hydroxyl Group." Tetrahedron, 57 (2001), 5707-5713.

Gerotto, et al., Effect of retreatment with interferon alone or interferon plus ribavirin on hepatitis C virus quasispecies diversification in nonresponder pateinets with chronic hepatitis C. Journal of Virology, Sep. 1999, vol. 73, No. 9, p. 7241-7247.

Giradet, et al., "Synthesis and Cytotoxicity of 4-Amino-5-oxopyrido[2,3-d]pyrimidine Nucleosides." Journal of Medicinal Chemistry (2000), 43(20), 3704-3713.

Gretch, D.R., "Use and interpretation of HCV diagonostic tests in the clinical setting." Clinics in Live Disease, Nov. 1997, vol. 1, No. 3, pp. 547-557.

Grouiller, et al., "Novel-p-toluensesulfaonylation and Thionocarbonylation of Unprotected Thymine Nucleosides," Synlett, 1993. 221-222 (1993).

Grouiller et al., "Structural studies on a psicofuranosyl nucleoside, a potential antiviral agent." J. Pharm. Belg., 47(4), 381-3 (1992).

Grunnagel, et al., "Preparation of D-Tagatose." Justus Liebigs Annalen der Chemic (1969), 721: 234-5.

Gunic, E., et al, "Synthesis and cytotoxicity of 4'-C-and 5'-C-substituted Toyocamycins," *Bioorg. Med. Chem.*, 9:163-170 (2001).

Haraguchi, et al., "Preparation and Reactions of 2'-and 3'-Vinyl Bromides of Uracil Nucleosides: Versatile Synthons for Anti-HIV Agents," Tetrahedron Letters, 32(28): 3391-94 (1991).

Haraguchi, et al., "Stereoselective Synthesis of 1'-C-Branched Uracil Nucleosides from Uridine," Nucleotides & Nucleosides, 14(3-5): 417-420 (1995).

Harry-O'Kuru, et al., "2'-C-alkylribonucleosides: Design, Synthesis and Conformation," Nucleosides & Nucleotides. vol. 16: 1457-60 (1997).

Harry-O'Kuru,, et al., "A short flexible route toward 2'—C-branched ribonucleosides," Journal of Organic Chemistry, American Chemical Society. Easton, US, vol. 62, No. 6, 1997, pp. 1754-1759.

Hassan, et al., "Nucleosides and Nucleotides 151: Conversion of (Z)-2'-(Cyanomethylene)-2'-Deoxyuridines into their (E)-Isomers via Addition of Thiophenol to the Cyanomethylene Moiety Followed by Oxidative Syn-elimination Reactions." J. Org. Chem., vol. 61, 1996, pp. 6261-6267.

Hassan, et al., "Nucleosides and Nucleotides 156: Chelation-Controlled and Nonchelation-Controlled Diastereofacial Selective Thiophernol Addition Reactions at the 2'-Position of 2'-[(Alkoxycarbonyl)methaylene]-2'-deoxyuridines: Conversion of (Z0-2'[(Alkoxycarbonyl)methylene]-2'-Deoxyuridines into their (E)-Isomers" J. Org. Chem., vol. 62, 1997, pp. 11-17.

Hattori, H. et al., "Nucleosides and Nucleotides 158" Journal of Medicinal Chemistry, American Chemical Society, vol. 39, 1996, pp. 5005-5001.

Hattori, H., et al., "Nucleosides and Nucleotides 175. Structural requirements of the sugar moiety for the antitumor activities of new nucleoside antimetabolites, 1-(3-C-ethynyl-b-D-ribo-pentofuranosyl)cytosine and -uracil," J. Med. Chem., 41: 2892-2902 (1998).

Hayakawa, et al., "Reaction of organometallic reagents with 2'- and 3'-ketouridine derivatives: synthesis of uracil nucleosides branched at the 2'- and 3'-positions." Chemical & Pharmaceutical Bulletin (1987), 35(6), 2605-8.

Hoard, D.E., et al., "Conversion of Mono- and Oligodeoxyribonucleotides to 5'-Triphosphates," J. Am Chem. Soc., 87(8):1785-1788 (Apr. 20, 1965).

Hodge, et al., "Amadori Rearrangement Products." Methods in Carbohydrate Chemistry (1963), 2: 99-107.

Holy, A., "Nucleic Acid Components and Their Analogs. CLIII. Preparation of 2'-deoxy-L-Ribonucleosides fo the Pyrimidine Series," Collect. Czech. Chem. Commun., 37(12): 4072-4087 (1972).

Hossain, et al., "Synthesis of 2'- and 3'-Spiro-isoxazolidine Derivatives of Thymidine & Their Conversions to 2',3'-dideoxy-2', 3'-didehydro-3'-C-substituted nucleosides by Radical Promoted Fragmentation," Tetrahedron vol. 49, No. 44, pp. 10133-10156, (1993).

Hostetler, K.Y., et al., "Greatly enhanced inhibition of Human Immunodeficiency Virus Type I replication in CEM and HT4-6C cells by 3'-deoxythymidine diphosphate dimyristoylglycerol, a lipid prodrug of 3'-deoxythymidine," Antimicrob. Agents Chemother., 36:2025.2029 (Sep. 1992).

Hostetler, K.Y., et al., "Synthesis and antiretroviral activity of phospholipids analogs of azidothymidine and other antiviral nucleosides," J. Biol. Chem., 265:6112-6117 (1990).

Hrebabecky, et al., "Nucleic Acid Components and their Analogs: CXLIX: Synthesis of Pyrimidine Nucleosides Derived from 1-Deoxy-D-Psicose," Coll Czech Chem Com, 37: 2059-2065 (1972).

Hrebecky, et al., "Synthesis of 7- and 9b-D-Psicofuranosylguanine and Their 1'-Deoxy Derivatives." Collection Czechoslov. Chem. Commun., vol. 39, 1974, pp. 2115-2123.

Hu, et al., Viral, host and interferon-related factors modulating the effect of interferon therapy for hepaptitis C virus infection. Journal of Viral Hepatitis, 2001, vol. 8, p. 1-18.

Hunston, R.N., et al., "Synthesis and biological properties of some cyclic phosphotriesters drived from 2'-deoxy-5-fluorouridine," J. Med Chem. 27:440-444 (1984).

Iglesias, et al., "Complete and Regioselective Deacetylation of Peracetylated Uridines Using a Lipase." Biotechnology Letters 22: 361-365, 2000.

Iimori, et al., "2'-C-, 3'-C-, and 5'-C-Methylsangivamycins: conformational lock with the methyl group." Tetrahedron Letters (1991), 32(49), 7273-6.

Iimori, et al., "A study on conformationally restricted sangivamycins and their inhibitory abilities of protein kinases." Nucleic Acids Symposium Series (1992), 27(Nineteenth Symposium on Nucleic Acids Chemistry, 1992), 169-70.

Iino, T., et al., "Nucleosides and nucleotides 139. Stereoselective synthesis of (2' S)-2'-C-alkyl-2'-deoxyuridines," Nucleosides & Nucleotides, 15(1-3): 169-181 (1996).

Ikegashira, K., et al., "Discovery of conformationally constrained tetracylic compounds as potent hepatitis C virus NS5B RNA polymerase inhibitors," Journal of Medicinal Chemistry, (Nov. 30, 2006) vol. 449, No. 24, pp. 6950-6953.

Imai, K., et al., "Studies on Phosphorylation. IV. Selective Phosphorylation of the Primary Hydroxyl Group in Nucleosides." J. Org. Chem., 34(6): 1547-1550 (Jun. 1969).

Itoh, et al., "Divergent and Sterocontrolled Approach to the Synthesis of Uracil Nucleosides Branched at the Anomeric Position," J Org Chem, 60(3): 656-662 (1995).

Johnson, C.R., et al., "3'—C-Trifluoromethyl ribonucleosides," Nucleosides & Nucleotides, vol. 14, 1995, pp. 185-194.

Jones, G. H., et al., "4'-substituted nucleosides. 5. Hydroxymethylation of nucleoside 5'-aidehydes," J. Org. Chem., 44:1309-1317 (1979).

Jones, G. H.; Moffatt, J. G., Methods in Carbohydrate Chemistry; Whisler, R. L. and Moffatt, J. L. Eds; Academic Press: New York, 1972; 315-322.

Kakefuda, et al., "Nucleosides and nucleotides. 120. Stereoselective radical deoxygenation of tert-alcohols in the sugar moiety of nucleosides: synthesis of 2',3'-dideoxy-2'-C-methyl- and -2'-C-ethynyl-b-D-threo-pentofuranosyl pyrimidines and adenine as potential antiviral and antitumor agents." Tetrahedron (1993), 49(38), 8513-28.

Kamaike, K., et al., "An efficient method for the synthesis of [4-15N]cytidine, 2'-deoxy[4-15N]cytidine, ]6-15N]adenosine, and 2'-deoxy[6-15N]adenosine derivatives," Nucleosodies and Nucleotides, 15(1-3_: 749-769 (1996).

Kaneko, M., et al., "A convenient synthesis of cytosine nucleosides," Chem. Pharm. Bull., 20:1050-1053 (1972).

Kawana, et al, "The Deoxygenatio of Tosylated Adenosine Derivatives with Grignard Reagents," Nucleic Acids Symp Ser, 17:37-40 (1986).

Kempe, T., et al., "Selective 2'-Benzoylation at the Cis 2', 3'-diols of Protected Ribonucleosides. New Solid Phase Synthesis of RNA and DNA-RNA Mixtures," Nucleic Acids Res., 10(21):6695-6714 (Nov. 11, 1982).

Kerr, S.G., et al., "N-(Dialkylamino)Methylene Derivatives of 2'-Deoxycytidine and Arabinocytidine: Physicochemical Studies for Potential Prodrug Applications," J. Pharm. Sci., 83(4): 582-586 (Apr. 1994).

Khamnei, S., "Neighboring group catalysis in the design of nucleotide prodrugs," J. Med Chem., 39:4109-4115 (1996).

Kim, et al., "A Novel Nucleoside Prodrug-Activating Enzyme: Substrate Specificity of Biphenyl Hydrolase-like Protein," Molecular Pharmaceutics (2004), 1(2), 117-127.

Klumpp, et al., "The Novel Nucleoside Analog R1479 (4'-Azidocytidine) is a Potent Inhibitor of NS5B-dpendent RNA Synthesis and Hepatits C Virus Replication in Cell Culture." The Journal of Biological Chemistry, vol. 281, No. 7, pp. 3793-3799, Feb. 17, 2006.

Kohn, et al., "A new method for the synthesis of furanose derivatives of aldohexoses," J Am. Chem. Soc., 1965, 87(23): 5475-80.

Kotra, L., et al., "Structure-Activity Relationships of 2'-Deoxy-2',2'-difluoro-L-erythro-pentofuranosyl Nucleosdes." J. Med. Chem. 1997, 40, 3635-3644.

Kucera, L.S., et al., "Novel membrane-interactive ether lipid analogs that inhibit infectious HIV-1 production and induce defective virus formation," AIDS Res. Hum. Retro Viruses, 6.491-501 (1990).

Kuhn, R., et al., "Uber eine molekulare Umlagerung von N-Glucosiden." Jahrg. 69, 1936, p. 1745-1754.

Kurtzberg J., et al, "Differential, toxicity of carbovir and AZT to human bone marrow hematopoietic progenitor cells in vitro," Exp. Hematol., 18(10):1094-1096 (1990).

Lai, V.C.H., et al., "Mutational analysis of bovine viral diarrhea virus RNA-dependant RNA polymerase," J. Virol., 73(12):10129-101136 (Dec. 1999).

Landowski, "Nucleoside ester prodrug substrate specificity of liver carboxylesterase," Journal of Pharmacology and Experimental Therapeutics (2006), 316(2), 572-580.

La Vaire, S., et al., "3'-deoxy-3'-C-trifluoromethyl nucleosides: Synthesis and antiviral evaluation," Nucleosides & Nucleotides, 17(12): 2267-2280 (1998).

Le Pogam, et al., "In Vitro Selected Conl Subgenomic Replicons Resistant to 2'-C-Methyl-Cytidine or to R1479 Show Lack of Cross Resistance." Virology 351 (2006), 349-359.

Le Pogam, et al., "Selection and Characterization of Replicon Variants Dually Resistant to Thumb- and Palm-Binding Nonnucleoside Polymeras Inhibitors of the Hepatitis C Virus." Journal of Virology, vol. 80, No. 12, Jun. 2006, p. 6146-6154.

Leonard, N. J., et al., "5-Amino-5-deoxyribose derivatives. Synthesis and use in the preparation of "reversed" nucleosides" *J. Heterocycl. Chem.*, 3:485-489 (Dec. 1966).

Lerza, R, et al., "In vitro synergistic inhibition of human bone marrow hemopoietic progenitor growth by a 3'-azido-3'-deoxy-thymidine, 2',3'-dideoxycytidine combination," *Exp. Hematol.*, 25(3):252-255 J (1997).

Lewis W, et al., "Zidovudine induces molecular, biochemical, and ultrastructural changes in rat skeletal muscle mitochondria," *J. Clin. Invest.*, 89(4):1354-1360 (1992).

Lewis, L. D., et al., "Ultrastructural changes associated with reduced mitochondrial DNA and impaired mitochondrial function in the presence of 2'3'-dideoxycytidine," *Antimicrob. Agents Chemother.*, 36(9):2061-2065 (1992).

Lewis, W., et al., "Fialuridine an dits metabolites inhibit DNA polymerase γ at sites of ultiple adjacent analog incorporation, decrease mtDNA abundance, and cause mitochondrial structural defects in cultured hepatoblasts," *Proceedings of the National Academy of Sciences*, USA, 93(8): 3592-7 (1996).

Leyssen, P., et al., "Perspectives for the treatment of infections with Flaviviridae," Clinical Microbiology Reviews (Washington D.C.) 13(1): 67-82 (Jan. 2000).

Li, et al., "2'—C-Branched ribonucleosides. 2. Synthesis of 2'—-C-beta-trifluormethyl pyrimidine ribonucleosides," Org. Lett., vol. 3, 2001, pp. 1025-1028.

Lin, T.S., et al., "Synthesis of Several Pyrimidine L-Nucleoside Analogues as Potential Antiviral Agents." Tetrahedron Letters, 51(4): 1055-1068 (1995).

Lohmann V., et al., "Biochemical and kinetic analyses of NS5B RNA-dependent RNA polymerase of the Hepatitis C virus," *Virology*, 249,108-118 (1998).

Lopez Aparicio, F.J., et al., "Synthesis of Saccarinic Acid Derivatives," Carbohydrate Res., 129:99 (1984).

Lopez-Herrera, F.J., et al., "A New Synthesis of 2-C Methyl-D-Ribono-1, 4-Lactone and the C-(/C-13 Fragment of Methynolide," J. Carbohydrate Chemistry, 13(5): 767-775 (1994).

Luh, T.-Y., et al., "A convenient method for the selective esterification of amino-alcohols," *Synthetic Communications*, 8(5):327-333 (1978).

Maga, Giovanni, et al., Lack of stereospecificity of suid pseudorabies virus thymidine kinase, Biochem. J., 294(2): 381-385 (1993).

Mahmoudian, M., et al., "A Versatile Procedure for the Generation of Nucleoside 5'-Carboxylic Acids Using Nucleoside Oxidase," Tetrahedron, Elsevier Science Publishers Amsterday, NL, vol. 54, No. 28, 8171-8182 Jul. 9, 1998.

Mansour, T.S., et al., "Editorial," Anti-Ineffective Agents in Medicinal Chemistry, (2007) vol. 6, No. 1, pp. 1.

Markland W., et al., "Broad-spectrum antiviral activity of the IMP dehydrogenase inhibitor VX-497: a comparison with ribavirin and demonstration of antiviral additivity with alpha interferon," Antimicrobial Agents and Chemotherapy, Apr. 2000, vol. 44, No. 4, pp. 859-866.

Martin, J., et al., Synthesis and Antiviral Activity of Monofluoro and Difluoro Analogues of Pyrimidine Deoxyribonucleosides Against Human Immnodeficiency Virus (HIV-1). J. Med. Chem. 1990, 33, 2137-2145.

Martin, X., et al., "Intramolecular hydrogen bonding in primary hydroxyl of thymine 1-(1-deoxy-β-D-piscofuranosyl)nucleoside," Tetrahedron, 50(22): 6689-6694 (1994).

Matsuda, et al., "Alkyl Addition Reaction of Pyrimidine 2'-Ketaonucleosides: Synthesis of 2'-Branched-Chain Sugar Pyrimidne Nucleosides (Nucleosides and Nucleotides. LXXXI)" Chem Pharm Bull, vol. 36(3):945-53 (1988).

Matsuda, et al., "Nucleosides and Nucleotides 104. Radical and Palladium-Catalyzed Deoxygenation of the Allylic Alcohol Systems in the Sugar Moiety of Pyrimidine Nucleosides." Nucleosides & Nucleotides, Dekker, New York, NY, U.S., vol. 11, No. 2/4, 1992, pp. 197-226.

Matsuda, et al., "Nucleosides and Nucleotides 94. Radical deoxygenation of tert-alcohols in 1-(2-C-alkylpentafuranosyl) pyrimidines: Synthesis of (2'S)-2-deoxy-2'-C-methylcytidine, and antileukemic nucleoside," Journal of Medicinal Chemistry, American Chemical Society Washington, US, vol. 34, 1991, pp. 234-239.

Matsuda, et al., "Radical deoxygenation of tert-alcohols in 2'—branched-chain sugar pyrimidine nucleosides: synthesis and antileukemic activity of 2'—deoxy-2' (S)-methylcytidine," Chem. Pharm. Bull., vol. 35, 1987, pp. 3967-3970.

McCormick, J., et al., "Structure and Total Synthesis of HF-7, a Neuraoactive Glyconucleoside Disulfate from the Funnel-Web Spider *Hololena curta*," Journal of the American Chemical Society, 1999, vol. 121, pp. 5661-5665.

McFarlin, et al., "The Reaction of Lithium Aluminum Hydride with Alcohols. Lithium Tri-t—butoxyaluminohydride as a New Selective Reducing Agent," J. Am. Chem. Soc. 1958, 80, 5372-76.

McKenzie, R., et al., "Hepatic failure and lactic acidosis due to fialuridine (FIAU), an investigational nucleoside analogue for chronic hepatitis B", *N. Engl. J. Med.*, 333(17):1099-1105 (1995).

Medina, D, J., et al., "Comparison of mitochondrial morphology, mitochondrial DNA content, and cell viability in cultured cells treated with three anti-Human immunodeficiency Virus dideoxynucleosides," *Antimicrob. Agents Chemother.*, 38(8):1824-8 (1994).

Meier, C., et al., "Cyclic saligenyl phosphotriesters of 2',3'-dideoxy-2',3'-didehydrothymidine (d4T)—A new pro-nucleic approach." *Bioorganic & Med. Chem. Letters* 7(2):99-104 (1997).

Meyer, R.B., Jr., et al., "2'-O-Acyl-6-thioinosine cyclic 3',5'-phosphates as prodrugs of thioinosinic acid," *J. Med. Chem.* 22: 811-815 (1979).

Mikhailov, S.N., et al., "Hydrolysis of 2'- and 3'-C-methyluridine 2'-, 3'-monophosphates and Interconversion and dephosphorylation of the resulting 2'- and 3'-monophosphates: Comparison with the reactions of Uridine monophosphates," J. Org. Chem., vol. 57: 4122-26 (1992).

Mikhailov, S.N., et al., "Substrate properties of C'-methylnucleoside and C'-methyl-2'-deoxynucleoside 5'-triphosphates in RNA and DNA synthesis reactions catalysed by RNA and DNA polymerases," Nucleosides & Nucleotides, 10(1-3): 339-343 (1991).

Mikhailov, S.N., et al., "Synthesis and properties of 3'—C-methylnucleosides and their phosphoric esters," Carbohydrate Research, vol. 124, 1983, pp. 75-96.

Miles, et al., "Circular Dichroism of Nucleoside Derivatives. IX. Vicinal Effects on the Circular Dichrosim of Pyrimidine Nucleosides." J. Am. Chem. Soc. 92(13): 3872-3881 (1970).

Moiseyev, et al., "Determination of the nucleotide conformation in the productive enzyme-substrate complexes of RNA-depolymerases." FEBS Letters (1997), 404(2,3), 169-172.

Moore, et al., "Synthesis of Nucleotide Analogues That Potently and Selectively Inhibit Human DNA Primase." Biochemistry (2002), 41(47), 14066-14075.

Murai, et al. "A synthesis and an x-ray analysis of 2'-C-,3'-C- and 5'-C-methylsangivamycins," Heterocycles (1992), 33(1), 391-404.

Neidlein, R., et al., "Mild preparationof I-benzyuloxyiminoalkylphosphonic dichlorides: Application to the synthesis of cyclic phosphonic diesters and cyclic monoester amides," *Heterocycles* 35:1185-1203 (1993).

Nishiguchi, S., et al., "Methods to Detect Substitutions in the Interferon-Sensitivity-Determining Region of Hepatitis C virus 1b for Prediction of Response to Interferon Therapy," Hepatology. Jan. 2001, vol. 33, No. 1, pp. 241-247.

Nishimura, T. et al. "Studies on Sythetic Nuclesides. Trimethylsilyl Derivatives of Pyrmidine and Purines," Chemical & Pharmaceutical Bulletin (1964), vol. 12, pp. 352-356.

Novak, J.J.K. & Sorm, F., "Nucleic Acid Components and Their Analogues. CXX. 2-C-Methyl-D-Ribose and Its Derivatives," Collection Czechoslav. Chem. Commun., 34:857-866 (1969).

Novak, J.J.K., "Chiroptical Properties of 2-Methyl-1,4-Lactones; Revised Absolute Configuration of 2-Deoxy-2-C-Methyl-Erythro-D-Pentono-1, 4-Lactones," Collection Czechoslav. Chem. Commun., 39:869-882 (1974).

Nutt, R. F., et al. "Branched-chain sugar nucleosides. III. 3'-C-methyladenine," J. Org. Chem. 33:1789-95 (1968).

Oivanen, M., et al., "Additional evidence for the exceptional mechanism of the acid-catalyzed hydrolysis of 4-oxopyrimidine nucleosides: Hydrolysis of 1-(1-alkoxyalkyl)uracils, seconucleosides, 3'-C-alkyl nucleosides and nucleoside 3', 5'-cyclic monophosphates," J. Chem. Soc. Perkin Trans. 2, 1994: 309-314 (1994).

Olsen et al. (Oral Session V, Hepatitis C Virus, Flaviviridae; 16th International Conference on Antiviral Research (Apr. 27, 2003, Savannah, Ga.) p. A76).

Ong, S.P., et al., "Synthesis of 3'—C-methyladenosine and 3'—C-methyluridine diphosphates and their interaction with the ribonucleoside diphosphate reductase from *Corynebacterium nephridii*," Biochemistry, vol. 31, 1992, pp. 11210-11215.

Pagliaro, L., et al., "[Hepatology: Old, recent and (maybe) future stories. A narrative review]. Epatologia: IERI, Oggle (Forse) Domani," Recenti Progressi in Medicina, (2006) vol. 97, No. 12, pp. 741-750.

Pan-Zhou, X-R, et al., "Differential effects of antiretroviral nucleoside analogs on mitochnodrial function in HepG2 cells," Antimicrob Agents Chemother 2000; 44:496-503.

Piantadosi, C., et al., "Synthesis and evaluation of novel ether lipid nucleoside conjugates for anti-HIV-1 activity," *J. Med. Chem.* 34:1408-1414 (1991).

Pierra, C., et al., "Comparative Studies of Selected Potential Prodrugs of B-L-dC, A Potent and Selective Anti-HBV Agent," Antiviral Res., 50:A79 (2001), Abstract No. 138.

Pierra, C., et al., "NM 283, and efficient prodrug of the potent anti-HCV agent 2'-C-methylcytidine," Nucleosides, Nucleotides and Nucleic Acids (2005), 24(5-7), 767-770.

Pierra, C., et al., "Synthesis and Pharmacokinetics of Valopicitabine (NM283), and Efficient Prodrug of the Potent Anti-HCV Agent 2'-C-Methylcytidine," Journal of Medicinal Chemistry (2006), 49(22), 6614-6620.

Reist, et al., "Potential anticancer agents. LXXVII. Synthesis of nucleosides of purine-6-thiol(6-mercaptopurine) containing "fraudulent" sugars." Journal of Organic Chemistry (1962), 27 3279-83.

Richman, D.D., et al., "The toxicity of azidothymidine (AZT) in the treatment of patients with AIDS and AIDS-Related Complex," *N. Engl. J. Med.*, 317(4):192-197 (1987).

Robins, et al., "Purine Nucleosides. XXIX. The Synthesis of 2'-Deoxy-L-adenosine and 2'-Deoxy-L-guanosine and Their [alpha] Anomers," Journal of Organic Chemistry, 35(3), 636-639 (Mar. 1970).

Rong, et al., "The Synthesis and Conformation of 2'-and 3'-Hypermodified Tricyclic Nucleosides and Their Use in the Synthesis of Novel 2'- or 3'-Isomeric 4(7)-Substituted Isoxazolidine-nucleosides," Tetrahedron vol. 50, No. 16, pp. 4921-4936. (1994).

Roque-Afonso, AM, et al., "Performance of Trugene hepatitis C virus5' noncoding genotyping kit, a new CLIP sequencing-based assay for hepatitis C virus genotype determination," Journal of Viral Hepatitis. Sep. 2002, vol. 9, Issue 5, pp. 385-389.

Rosenthal, et al., "Branched-chain sugar nucleosides. Synthesis of 3'—C-ethyl (and 3'—C-butyl) uridine," Carbohydrate Research, vol. 79, 1980, pp. 235-242.

Sakthivel, et al. "Electrophilic fluorination of 5-(cyanomethyl)imidazole-4-carboxylate nucleosides: Facile entry to 3-fluoro-3-deazaguanosine analogues." Synlett (2005), (10), 1586-1590.

Sakthivel, et al., "Direct SNAr animation of fluorinated imidazo[4,5-c]pyridine nucleosides: efficient syntheses of 3-fluoro-3deazaadenosine analogs." Tetrahedron Letters (2005), 46(22), 3883-3887.

Salidino, R., et al., "A new and efficient synthesis of cytidine and adenosine derivatives by dimethyldioxirane oxidation of thiopyrimidine and thiopurine nucleosides," J. chem. Soc., Perkin Trans. I., 21: 3053-3054 (1994).

Samano, et al., "Nucleic Acid Related Compounds. 77. 2',3'-Didehydro-2', 3'-Dideoxy-2' (and 3')-Methylnucleosides Via [3,3]-Sigmatropic Rearrangements of 2'(and 3')-Methylene-3'(and 2')-O-Thiocarbonyl Derivatives and Radical Reuction of a 2'-Chloro-3'Methylene Analogue," Can. J. Chem., 71: 186-191 (1993).

Samano, et al., "Synthesis and Radical-Induced Ring-Opening Reactions of 2'-Deoxyadenosine-2'-Spirocyclopropane and its Uridine analogue. Mechanistic Probe for Ribonucleotide Reductases," J Am Chem Soc, 114: 4007-08 (1992).

Sandhu, et al., "Evaluation of microdosing strategies for studies in preclinical drug development: Demonstration of linear pharmacokinetics in dogs of a nucleoside analog over a 50-fold dose range." Drug Metabolism and Disposition (2004), 32(11), 1254-1259.

Sato, et al., "C-Nucleoside synthesis. 10. Synthesis of 2'-methylated pyrimidine C-nucleosides." Tetrahedron Letters (1980), 21(20), 1971-4.

Sato, et al., "C-Nucleoside synthesis. 19. Stereocontrolled general synthesis of pyrimidine C-nucleosides having branched-chain sugar moieties." Bulletin of the Chemical Society of Japan (1983), 56(9), 2680-99.

Savochkina, et al., "Substrate properties of c—methylnucleoside triphosphates in RNA syntheses catalyzed by *E. coli* RNA—polymeruse" Molecular Biology, 1989, v. 23, No. 6.

Scheibler, C., "Ueber das Saccharin und die Saccharinsaure," Chemische Berichte, 13:2212-2217 (1880). In German.

Schiff, E.R., "Emerging strategies for pegylated interferon combination therapy," Nature Clinical Practice Gastoenterology and Hepatology, (2007) vol. 4, No. Suppl. 1, pp. S17-S21.

Schmit, C., et al., "Synthesis of 2'-Deoxy-2'—Alpha-Monofluoromethyl and Trifluoromethylnucleosides," Synlett, Thieme Verlag, Stuttgart, DE, No. 4, 1994, pp. 241-242.

Schmit, C., et al., "The effects of 2'- and 3'-alkyl substituents on oligonucleotide hybridization and stability," Bioorg. & Med. Chem. Lett., 4(16): 1969-1974 (1994).

Serafinowski, P.J., et al., "New method for the preparation of some 2'- and 3'-trifluoromethyl-2',3'-dideoxyuridine derivatives," Tetrahedron, 56(2):333-339 (1999).

Shalaby, et al., "Conformations and Structure Studies of Sugar Lactones in the Solid State. Part 11. The Molecular Structure of a-D-Glucosaccharino-Y-Lactone: 2-C-Mehtyl-D-Ribo-Pentono-1,4-lactone." Carbohydrate Research (1994), 264(2), 191-8.

Sharma, et al., "Synthesis of 3'—Trifluoromethyl Nucleosides as Potential Antiviral Agents," Nucleosides, Nucleotides and Nucleic Acids, Marcel Dekker, Ann Harbor, MI, US, vol. 19, No. 4, 2000, pp. 757-774.

Shi, et al., Synthesis and in vitro Anti-HCV Activity of β-d- and 1-2'-Deoxy-2'-Fluororibonucleosides, Nucleosides, Nucleotides & Nucleic Acids 2005, vol. 23, Nos. 5-7, pp. 875-879.

Shim, Jae II., "Recent patents on nucleoside and nucleotide inhibitors for HCV," Recetn Patents on Anti-Infective Drug Discovery (2006), 1(3), 323-331.

Sinko, et al., Carrier-Mediated Intestinal Absorption of Valacyclovir, the L-Valyl Ester Prodrug of Acyclovir. Biopharmaceutics & Drug Disposition 1998, vol. 19, pp. 209-217.

Sinkula et al., "Rationale for design of biologically reversible drug derivatives: prodrugs," *J. Pharm. Sci.*, 1975,64: 181-210.

Smith, et al., "Synthesis of new 2'-b-C-methyl related triciribine analogues as anti-HCV agents." Valeant Pharmaceuticals International, Costa Mesa, CA, USA. Bioorganic & Medicinal Chemistry Letters (2004), 14(13), 3517-3520.

Sommadossi J-P., et al., "Comparison of cytotoxicity of the (−)- and(+)-enantiomer of 2',3'-dideoxy-3'-thiacytidine in normal human bone marrow progenitor cells," Biochemical Pharmacology 1992; 44:1921-1925.

Sommadossi J-P., et al., "Toxicity of 3'-azido-3'-deoxythymidine and 9-(1-3-dihydroxy-2-propoxymethyl)guanine for normal human hematopoietic progenitor cells in vitro" Antimicrobial Agents and Chemotherapy 1987; 31:452-454.

Song, et al., Amino Acid Ester Prodrugs of the Anticancer Agent Gemcitabine: Synthesis, Bioconversion, Metabolic Bioevasion, and hPEPT1-Medicated Transport, Moleculare Pharmaceutics (2005), 2(2), 157-167.

Sorbera, L.A., et al., "Valopicitabine: anti-hepatitis C virus drug RNA—directed RNA polymerase (NS5B) inhibitor," Drugs of the Future (2006), 31 (4), 320-324.

Sowden, J., "The Saccharinic Acids," Adv. Carbohydrate Chem., 12:43-46 (1957).

Spardari, et al., "L-Thmidine is Phosphorylated by Herpes Simplex Virus Type 1 Thymidine Kinase and Inhibits Viral Growth," Journal of Medicinal Chemistry, 35(22), 4214-4220 (1992).

Standring, D.N., et al., "Antiviral Beta-L-Nucleosides Specific for Hepatitis B Virus Infection," Antiviral Chem. & Chemother., 12 (Suppl. 1): 119-129 (2001).

Starrett, J.E.Jr., et al., "Synthesis, oral bioavailability determination, and in vitro evaluation of prodrugs of the antiviral agents 9-(2-(phosphonomethoxy)ethylladenine (PMEA)," J. Med Chem. 37:1857-1864 (1994).

Stuyver, et al., "Ribonucleoside Analogue That Block Replication of Bovine Viral Diarrhea and Hepatits C Viruses in Culture." Antimicrobial Agents and Chemotherapy, vol. 47, No. 1, Jan. 2003, p. 244-254.

Sundberg, et al., Advanced Organic Chemistry, Part b, 1990, pp. 232 and 236.

Takenuki, et al., "Nucleosides and nucleotides. XLIII. On the stereoselectivity of alkyl addition reaction of pyrimidine 2'-ketonucleosides." Chemical & Pharmaceutical Bulletin (1990), 38(11), 2947-52.

Tang, X.-Q., et al., "2'-C-Branched Ribonucleosides: Synthesis of the Phophoramidite Derivatives of 2'-C-B-Methylcytidine and Their Incorporation into Oligonucleotides," J. Org. Chem., 64(3): 747-754 (1999).

The Merck Index, 12th edition, 1996, p. 275.

Tritsch, D., et al., "3'-β-ethynyl and 2'-deoxy-3'-β-ethynyl adenosines: First 3'-β-branched adenosine substrates of adenosine deaminase," Bioorg. & Med. Chem. Lett., 10: 139-141 (2000).

Tronchet, et al. "72. Synthese et desamination enzymatique des C-hydroxymethyl-3'-et C-methyl-3'—beta-D-xylofurannosyl-9-adenines," Helv. Chim. Acta, vol. 62, 1979, pp. 689-695.

Tunitskaya, V.L., et al., "Substrate properties of C'-methyl UTP derivatives in T7 RNA polymerase reactions. Evidence for N-type NTP conformation," FEBS Letters, 400: 263-266 (1997).

Tyrsted, G., et al., "Inhibition of the synthesis of 5-phosphoribosyl-1-pyrophosphate by 3'-deoxyadenosine and structurally related nucleoside analogs," Biochem. Biophys. Acta., 155(2): 619-622 (Feb. 26, 1968).

Usui, H., et al., "Synthesis of 2'-deoxy-8,2'-ethanoadenosine and 3'-deoxy-8,3'-ethanoadenosine (Nucleotides & Nucleosides. LXIV)," Chem. Pharm. Bull., 34(1):15-23 (1986).

Vassilev, V., et al., "Bovine Viral Diarrhea Virus Induced Apoptosis Correlates with Increased Intracellular Viral RNA Accumulation." Virus Research, 69: 95-107 (2000).

Velazquez, et al., "Synthesis of '1-'3',5'-bis-0-(tert-butyldimethylsily)-beta-D-arabino-and beta-D-ribofuransoyl !cytosine!-2'—spiro-5"-(4"-amino-1",2"-oxathiole-2",2"-dioxide). Analogues of the highly specific anti-HIV-1 agent TSAO-T," Tetrahedron, vol. 50, 1994, pp. 11013-11022.

Verri, A., et al., "Lack of enantiospecificity of human 2'-deoxycytidine kinase: relevance for the activetion of B-L-deoxyctidine analogs as antineoplastic and antiviral agents," Molecular Pharmacology, 51(1): 132-138 (Jan. 1997).

Verri, a., et al., "Relaxed Enantioselectivity of Human Mitochondrial Thymidine Knase and Chemotherapeutic Uses of L-Nucleoside Analogues," Biochem. J., 328(1): 317-320 (Nov. 15, 1997).

Von Buren, et al., "Branched oligodeoxynucleotides: automated synthesis and triple helical hybridization studies." Tetrahedron (1995), 51(31), 8491-506.

Von Janta-Lipiniski, M., et al., "Newly Synthesized L-Enantiomers of 3'-Fluoro-Modified B-2'-Deoxyribonucleoside 5'-Triphosphates Inhibit Hepatitis B DNA Polymerase but not the Five Cellular SNA Polymerases a, B, y, d and E Nor HIV-1 Reverse Transcriptase," J. Medicinal Chemistry, 41(12): 2040-2046 (May 21, 1998).

Wagner, D., et al., "Preparation and Synthetic Utility of Some Organotin Derivatives of Nucleosides," J. Org. Chem., 39(1):24-30 (1974).

Walczak, K., et al., "Synthesis of 1-(3-alkyl-2,3-dideoxy-D-pentofuranosyl)uracils with potential anti-HIV activity," Acta Chemica Scand., 45: 930-934 (1991).

Walton et al., "Branched-chain sugar nucleosides. A new type of biologically active nucleoside," J. Am. Chem. Soc., 88(19): 4524-25 (1966).

Walton, et al., "Branched-Chain Sugar Nucleosides: V. Synthesis and Antiviral Properties of Several Branched-Chain Sugar Nucleosides," Antiviral Nucleosides, vol. 12: 306-309 (1969).

Weinberg, R.S., et al., "Effect of antiviral drugs and hematopoietic growth factors on in vitro erythropoiesis," Mt. Sinai J. Med 1998;65(1):5-13.

Whistler, R. L., and BeMiller, J.N., "[118] 'a'-D-Glucosaccharino-1,4-Lactone," Methods in Carbohydrate Chemistry, 2:484-485 (1963).

Wohnsland, A., et al., "Viral determinants of resistance to treatment in patients with hepatitis C," Clinical Microbiology reviews, (2007) vol. 20, No. 1, pp. 23-38.

Wolf, et al., "New 2'—C-Branched-Chain Sugar Nucleoside Analogs With Potential Antiviral or Antitumor Activity," Synthesis, Georg Thieme Verlag. Stuttgart, DE, No. 8, Aug. 1992, pp. 773-778.

Wolfe, et al., Tetrahedron Letters, vol. 36(42): 7611-14 (1995).

Wu, et al., Targeting NS5B RNA-dependent RNA polymerase for anti-HCV chemotherapy. Current Drug Targets—Infectious Disorders 2003, vol. 3, p. 207-219.

Wu, et al., "A New Stereospecific Synthesis of [3.1.0] Cicyclic Cyclopropano Analog of 2',3'-Dideoxyuridine." Tetrahedron, vol. {16?} 46, 1990, pp. 2587-2592.

Yarchoan, R., et al. "Long-term toxicity / activity profile of 2',3'-dideoxyinusine in AIDS or AIDS-related complex," The Lancet, 336(8714):526-529 (1990).

Yoshida Y, et al., "Reversal of azidothymidine-induced bone marrow suppression by 2',3'-dideoxythymidine as studied by hemopoietic clonal culture," AIDS Res. Hum. Retroviruses, 6(7):929-932 (1990).

Zedeck et al., "Inhibition of the steroid induced synthesis of Δ5-3-ketosteroid isomerase in Pseudomonas testosteroni by a new purine deoxyribonucleoside analog: 6-chloro-8aza-9-cyclopentylpurine," Mol. Phys., 3(4):386-95 (1967).

Zemlicka, J., et al. "Aminoacyl Derivatives of Nucleosides, Nucleotides, and polynucleotides. VIII. The Preparation of 2'(3)—O-L-Phenylalanyluridine, -cytidenie, -Adensonine, -inosine, -guanosine and 2'-Deoxy-3' O-L-Phenylalanyladenosine," Collection Czecoslov, Chem. Commun. 1969, vol. 43, No. 13, 3755-3767.

Zemlicka, J., et al., "Substrate Specificity of Ribosomal Peptidyltransferase. Peditidyltranferase. Effect of Modifications in the Heterocyclic, Carbohydrate and Amino Acid Moiety of 2'(3)-O-L-Phenyladenosine." Biochemistry. Dec. 2, 1975, vol. 14, No. 24, 5239-5249.

Zhou, et al., Pharmacokinetics and pharmacodynamics of valopicitabine. Journal of Hepatology 2005, vol. 42 (Suppl. 2), p. 229.

Zinichenko, et al., "Substrate Specificity of Uridine and Purine Nucleoside Phosphorylases of the Whole Cells of Escherichia coli." Nucleic Acids Research, Symposium Series No. 18., 1987, pp. 137-140.

Zon, G., "Cyclophosphamide Analogues," Chapter 4 in Progress in Medicinal Chemistry, vol. 19, G.P Ellis and G.B. West, Eds., pp. 205-246 (1982).

Office Action dated Oct. 1, 2003 from U.S. Appl. No. 09/863,816.

Notice of Allowance dated Jun. 23, 2004 from U.S. Appl. No. 09/863,816.

Office Action dated Aug. 27, 2003 from U.S. Appl. No. 09/864,078.

Notice of Allowance dated Feb. 19, 2004 from U.S. Appl. No. 09/864,078.

Notice of Allowance dated May 17, 2005 from U.S. Appl. No. 10/602,135.

Office Action dated Apr. 5, 2005 from U.S. Appl. No. 10/602,135.

Notice of Allowance dated Mar. 9, 2006 from U.S. Appl. No. 10/602,136.

Office Action dated Jul. 28, 2006 from U.S. Appl. No. 10/602,142.

Office Action dated Sep. 20, 2007 from U.S. Appl. No. 10/602,142.

Office Action dated Dec. 10, 2008 from U.S. Appl. No. 10/602,142.

Office Action dated Nov. 15, 2005 from U.S. Appl. No. 10/602,142.

Office Action dated Mar. 29, 2007 from U.S. Appl. No. 10/602,142.

Office Action dated Feb. 26, 2008 from U.S. Appl. No. 10/602,142.

Office Action dated May 30, 2006 from U.S. Appl. No. 10/602,691.

Office Action dated Aug. 22, 2007 from U.S. Appl. No. 10/602,691.

Office Action dated Oct. 7, 2008 from U.S. Appl. No. 10/602,691.

Office Action dated Dec. 29, 2006 from U.S. Appl. No. 10/602,691.

Office Action dated Nov. 7, 2005 from U.S. Appl. No. 10/602,691.
Office Action dated Feb. 26, 2008 from U.S. Appl. No. 10/602,691.
Notice of Allowance dated Dec. 28, 2005 from U.S. Appl. No. 10/602,692.
Office Action dated Apr. 5, 2005 from U.S. Appl. No. 10/602,692.
Notice of Allowance dated Dec. 27, 2005 from U.S. Appl. No. 10/602,693.
Office Action dated Apr. 6, 2005 from U.S. Appl. No. 10/602,693.
Notice of Allowance dated Dec. 27, 2005 from U.S. Appl. No. 10/602,694.
Office Action dated Apr. 6, 2005 from U.S. Appl. No. 10/602,694.
Office Action dated Sep. 10, 2004 from U.S. Appl. No. 10/602,976.
Office Action dated May 19, 2005 from U.S. Appl. No. 10/602,976.
Notice of Allowance dated Oct. 13, 2005 from U.S. Appl. No. 10/602,976.
Office Action dated Aug. 15, 2006 from U.S. Appl. No. 10/608,907.
Office Action dated May 31, 2007 from U.S. Appl. No. 10/608,907.
Office Action dated Jan. 28, 2008 from U.S. Appl. No. 10/608,907.
Office Action dated Nov. 26, 2008 from U.S. Appl. No. 10/608,907.
Notice of Allowance dated Apr. 7, 2009 from U.S. Appl. No. 10/608,907.
Office Action dated Aug. 2, 2006 from U.S. Appl. No. 10/609,298.
Office Action dated Jul. 10, 2008 from U.S. Appl. No. 10/609,298.
Notice of Allowance dated Apr. 7, 2009 from U.S. Appl. No. 10/609,298.
Office Action dated Dec. 22, 2006 from the U.S. Appl. No. 10/735,408.
Office Action dated Aug. 21, 2007 from the U.S. Appl. No. 10/735,408.
Office Action dated Jan. 9, 2008 from the U.S. Appl. No. 10/735,408.
Office Action dated Sep. 24, 2008 from the U.S. Appl. No. 10/735,408.
Office Action dated Mar. 16, 2009 from the U.S. Appl. No. 10/735,408.
Notice of Allowance dated May 6, 2009 from the U.S. Appl. No. 10/735,408.
Office Action dated Oct. 5, 2005 from U.S. Appl. No. 11/005,440.
Office Action dated Dec. 5, 2006 from U.S. Appl. No. 11/005,440.
Office Action dated Jun. 13, 2007 from U.S. Appl. No. 11/005,440.
Office Action dated Oct. 16, 2007 from U.S. Appl. No. 11/005,440.
Office Action dated Aug. 21, 2006 from U.S. Appl. No. 11/005,441.
Notice of Allowance dated Jun. 22, 2007 from U.S. Appl. No. 11/005,441.
Notice of Allowance dated Jan. 8, 2008 from U.S. Appl. No. 11/005,441.
Office Action dated Aug. 7, 2006 from U.S. Appl. No. 11/005,442.
Office Action dated May 16, 2007 from U.S. Appl. No. 11/005,442.
Office Action dated Nov. 28, 2007 from U.S. Appl. No. 11/005,442.
Office Action dated Oct. 5, 2005 from U.S. Appl. No. 11/005,443.
Office Action dated Mar. 12, 2007 from U.S. Appl. No. 11/005,443.
Advisory Action dated Aug. 8, 2007 from U.S. Appl. No. 11/005,443.
Office Action dated Sep. 5, 2008 from U.S. Appl. No. 11/005,443.
Office Action dated Oct. 12, 2005 from U.S. Appl. No. 11/005,444.
Office Action dated Dec. 5, 2006 from U.S. Appl. No. 11/005,444.
Office Action dated Jun. 13, 2007 from U.S. Appl. No. 11/005,444.
Office Action dated Oct. 9, 2007 from U.S. Appl. No. 11/005,444.
Office Action dated Oct. 6, 2008 from U.S. Appl. No. 11/005,444.
Office Action dated Oct. 6, 2006 from U.S. Appl. No. 11/005,445.
Office Action dated Feb. 26, 2008 from U.S. Appl. No. 11/005,445.
Office Action dated Oct. 7, 2008 from U.S. Appl. No. 11/005,445.
Office Action dated Jul. 17, 2008 from U.S. Appl. No. 11/005,445.
Notice of Allowance dated Apr. 30, 2009 from U.S. Appl. No. 11/005,445.
Office Action dated Oct. 5, 2005 from U.S. Appl. No. 11/005,446.
Office Action dated Dec. 5, 2006 from U.S. Appl. No. 11/005,446.
Office Action dated Aug. 20, 2007 from U.S. Appl. No. 11/005,446.
Office Action dated Mar. 17, 2008 from U.S. Appl. No. 11/005,446.
Notice of Allowance dated Oct. 11, 2006 from U.S. Appl. No. 11/005,447.
Notice of Allowance dated Feb. 12, 2007 from U.S. Appl. No. 11/005,447.
Notice of Allowance dated Aug. 22, 2007 from U.S. Appl. No. 11/005,447.
Office Action dated Oct. 12, 2005 from U.S. Appl. No. 11/005,466.
Office Action dated Nov. 20, 2006 from U.S. Appl. No. 11/005,466.
Office Action dated Jun. 13, 2007 from U.S. Appl. No. 11/005,466.
Office Action dated Oct. 9, 2007 from U.S. Appl. No. 11/005,466.
Office Action dated Aug. 18, 2006 from U.S. Appl. No. 11/005,467.
Notice of Allowance dated Aug. 22, 2007 from U.S. Appl. No. 11/005,467.
Office Action dated Sep. 26, 2006 from U.S. Appl. No. 11/005,468.
Office Action dated Jun. 14, 2007 from U.S. Appl. No. 11/005,468.
Office Action dated Oct. 2, 2007 from U.S. Appl. No. 11/005,468.
Office Action dated Oct. 5, 2006 from U.S. Appl. No. 11/005,469.
Office Action dated Jul. 18, 2007 from U.S. Appl. No. 11/005,469.
Office Action dated Mar. 24, 2008 from U.S. Appl. No. 11/005,469.
Notice of Allowance dated Oct. 12, 2006 from U.S. Appl. No. 11/005,470.
Notice of Allowance dated Mar. 7, 2007 from U.S. Appl. No. 11/005,470.
Notice of Allowance dated Aug. 22, 2007 from U.S. Appl. No. 11/005,470.
Office Action dated Jul. 18, 2007 from U.S. Appl. No. 11/005,471.
Office Action dated Feb. 28, 2008 from U.S. Appl. No. 11/005,471.
Office Action dated Oct. 12, 2005 from U.S. Appl. No. 11/005,472.
Office Action dated Dec. 5, 2006 from U.S. Appl. No. 11/005,472.
Office Action dated Jun. 13, 2007 from U.S. Appl. No. 11/005,472.
Office Action dated Oct. 9, 2007 from U.S. Appl. No. 11/005,472.
Office Action dated Nov. 25, 2005 from U.S. Appl. No. 11/005,473.
Notice of Allowance dated Aug. 8, 2006 from U.S. Appl. No. 11/005,473.
Office Action dated Oct. 2, 2008 from U.S. Appl. No. 11/516,928.

* cited by examiner

PROCESS FOR PREPARING A SYNTHETIC INTERMEDIATE FOR PREPARATION OF BRANCHED NUCLEOSIDES

CROSS REFERENCE

This application claims priority to U.S. Provisional Application No. 60/753,507 filed Dec. 23, 2005, the disclosure of which is incorporated by reference.

FIELD OF THE INVENTION

This application relates to methods for the preparation of a synthetic intermediate in a process for preparing 2'-C-alkyl-2'-halo-nucleoside analogues, which are important as antiviral, anti-cancer, and antibacterial agents.

BACKGROUND OF THE INVENTION

A process for preparing a halogen-substituted ribonolactone intermediate that is useful in the synthesis of a 2'-C-methyl-2'-halo nucleoside analogue presents ongoing challenges, particularly where the halogen atom is fluorine.

A key intermediate in the preparation of sugar analogues used in the synthesis of nucleosides and vitamins is 2-C-methyl-D-ribono-lactone. As early as 1880, Scheibler described a process for preparing the lactone (John Sowden, "The Saccharinic Acids" in *Adv. Carbohydrate Chem.* 12:43-46 (1957), citing C. Scheibler, *Berichte* 13:2212 (1880)). Unfortunately, product yields were only approximately 10% (Id.). At about the same time, H. Kiliani synthesized 2-methyl-D-ribonolactone by treating D-fructose with calcium hydroxide (H. Kiliani, *Berichte*, 15:2953 (1882), as cited in F. J. Lopez-Herrera et al., *J. Carbohydrate Chemistry*, 13(5): 767-775 (1994)). However, the process required months to run to completion and product yield was also only approximately 10% (Id. at 768). Kiliani's process, however, enabled him to establish the positions of important functional groups on the compound (John Sowden, "The Saccharinic Acids" in *Adv. Carbohydrate Chem.* 12:43-46 (1957), citing H. Kiliani, *Ann.*, 213:361 (1883)).

In the early 1960s, Whistler and BeMiller attempted to improve upon Kiliani's synthesis (Roy L. Whistler and J. N. BeMiller, "α-D-Glucosaccharino-1,4-lactone" in *Methods in Carbohydrate Chemistry*, 2:484-485 (1963)). Whistler and BeMiller added boiling water and calcium hydroxide to D-fructose, flushed the system with nitrogen gas, and repeated the same process. The mixture then was maintained for 6-8 weeks, after which it was treated with $CO_2$ and oxalic acid dihydrate, and filtered under pressure. The residue washed repeatedly to a syrup-like consistency, and filtrates combined; solvent evaporated under reduced pressure and the resultant product allowed to crystallize under refrigeration. The final product yield was still only about 10% (Id. at 485) and the process took two months to complete.

BE 731271 and GB 1189973, assigned to Deutsche Akademie der Wissenchaften, disclosed a process for preparing 3'-fluoronucleosides by reacting a nucleoside with a fluorinating agent such as HF in an organic solvent like THF at temperatures ranging from 130-160° C.

In an attempt to improve product yields, Lopez-Aparicio et al. reported the synthesis of 2-C-methyl-D-ribono-1,4-lactone from 2,3-O-isopropylidene-D-glyceraldehyde as an alternative to the Kiliani synthesis (Lopez-Aparicio et al., *Carbohydrate Res.*, 129:99 (1984), as cited in F. J. Lopez-Herrera et al., *J. Carbohydrate Chemistry*, 13(5):767-775 (1994) at 768-769). The process of Lopez-Aparicio included condensing 2,3-O-isopropylidene-D-glyceraldehyde with (1-methoxy-carbonyl-ethylidene)triphenylphosphorane to produce methyl E-(S-4,5-dihydroxy-4,5-O-isopropylidene-2-methyl-2-pentenoate; hydrolyzing (in HCl) and photochemically isomerizing the pentenoate; lactonizing the pentenoate product to produce a butenolide; tritylating the butenolide at C-5 by reaction with trityl-chloride and pyridine, followed by cis-hydroxylation with potassium permanganate and methylene chloride in the presence of a crown ether. Final removal of the trityl(triphenylmethyl) group was achieved by reaction with TFA (trifluoroacetic acid) (Id. at 768). Lopez-Aparicio et al. reported product yields of ribonolactone at about 80%, but others were not able to reproduce this figure based on the gram mass amounts of materials provided in the experimental section of their publication. Instead, calculations indicated a percent yield of about 36% ribonolactone. In addition, the process of Lopez-Aparicio et al. was far more complex than the Kiliani synthesis, required the use of toxic reagents such as potassium permanganate and specialized equipment for irradiation to attain photochemical isomerization, and had a minimum of 60 hours reaction time (Id. at 768, 770-772).

None of the foregoing approaches addressed the problem of preparing 2'-C-branched or 2'-disubstituted ribonucleoside analogues.

In 1989, the Asahi Glass Company Ltd. reported the synthesis of fluoronucleosides that had antiviral and antitumor effects (JP 02270864 and JP 01100190). These nucleosides were prepared by treating a 9-(alpha-fluoro-4-beta-hydroxy-1-beta-cyclopentyl)pyrimidine derivative with trifluoromethanesulphonyl chloride, p-toluenesulphonyl chloride, methanesulphonyl chloride or imidazolylsulphonyl chloride in the presence of a base, followed by reduction (JP 02270864). In a second synthetic method, 2',3'-deoxy-2',3'-didehydro-2'-fluoronucleosides were obtained by the dehydrogenation of a 2'-deoxy-2'-fluororibofuranosyl derivative, or by dehydrogenation of a 2',3'-dideoxy-2'-fluoro-3'-halo-ribonucleoside derivative (JP 01100190).

In 1990, Bobek et al. disclosed the synthesis of antiviral, antitumor, and antimicrobial arabinopyranosyl nucleoside derivatives that had a fluorine atom at the 2'-position of the pyranose ring (U.S. Pat. No. 4,918,056). These compounds were prepared by the condensation of a pyrimidine, purine, or 1,3-oxazine nucleobase with an hydroxyl group-blocked, acylated 2-deoxy-2,2-difluoro-D-arabinopyranoside and/or an acylated 2-deoxy-2-bromo-2-fluoro-D-arabinopyranoside (Id.).

In 1997 Harry-O'Kuru et al. described a synthetic route for preparing 2'-C-branched ribonucleosides (Harry-O'Kuru et al., *J. Org. Chem.*, 62:1754-9 (1997)). Commercially available 1,3,5-tri-O-benzoyl-α-D-ribofuranose was used as the starting material, which was prepared from D-ribose or D-arabinose (D-arabinopyranose). The 1,3,5-tri-O-benzoyl-α-D-ribofuranose was oxidized at the free 2-OH with Dess-Martin periodinane reagent, and produced 1,3,5-tri-O-benzoyl-2-keto-ribofuranose as well as its corresponding hydrate. The desired product and hydrate were stirred with excess $MgSO_4$ and permitted to stand overnight. The mixture was then filtered and concentrated in order to produce a substantially pure ketone product. The resultant 2-ketosugar was treated with $MeMgBr/TiCl_4$ (or alternatively with $MeTiCl_3$, $CH_2$=$CHMgBr/CeCl_3$, or TMSC≡$CLi/CeCl_3$), which produced an anomeric mixture of the desired 1,3,5-tri-O-benzoyl-2-substituted alkyl-, alkenyl- or alkynyl-ribofuranoside and its transesterified isomers, α- and β-2,3,5-tri-O-benzoyl-2-substituted alkyl, alkenyl or alkynyl ribofuranoside in a nearly 5:3 ratio of desired product to isomeric forms (Id. at 1755). The 2-alkylated ribofuranosides then were converted to a single, desired product, 1,2,3,5-tetrabenzoyl-2-alkylribofuranoside, by treatment with benzoyl chloride, DMAP and triethylamine in a reported approximately 70% yield with a β/α ratio of 4:1 (Id.).

In 1998, Chambers et al. reported the synthesis of 2',3'-dideoxy-3'-fluorouridine compounds by reaction of a corresponding anhydronucleoside with hydrogen fluoride in the presence of an organo-iron compound and in an organic solvent (U.S. Pat. No. 5,717,086).

Recent reports of syntheses of 2' and/or 3' halonucleosides have been disclosed by Pharmasset, Inc., The University of Georgia Research Foundation, Inc., and Emory University.

WO 05/003147 (also US 2005/0009737) to Pharmasset, Inc., described the synthesis of 2'-C-methyl-2'-fluoro nucleoside analogues by one of two general synthetic routes: alkylating an appropriately modified carbohydrate compound, fluorinating it, and then coupling it to a desired nucleobase, or glycosylating a desired nucleobase to form a nucleoside, then alkylating the nucleoside, and finally fluorinating the preformed nucleoside. Pharmasset's first approach utilized a modified carbohydrate that was an hydroxyl group-protected lactone, which was alkylated with a reagent such as methyl lithium in an anhydrous solvent like THF, and then was reacted with a commercially available fluorinating agent like DAST or Deoxofluor, followed by a deprotection step. The reaction proceeded with inversion at the 2'-position such that the fluorine atom was in the "down" or ribo configuration. Pharmasset's second synthetic route comprised the modification of a commercially available nucleoside whose hydroxyl groups were protected by protective groups known in the art. The nucleoside was oxidized at the 2'-position to provide a 2'-ketone, and the 2'-ketone was reacted with an alkylating agent such as methyl lithium in THF at about 0° C. to afford a 2'(S) or 2'-methyl "down", 2'-hydroxyl "up" configured nucleoside tertiary alcohol. A fluorine atom then was introduced by reacting the nucleoside with a commercially available fluorinating reagent such as DAST in an anhydrous, aprotic solvent like toluene with inversion at the 2'-position to afford a 2'-C-methyl "up", 2'-fluoro "down" configuration of the nucleoside. However, by either synthetic route, Pharmasset's isolation and purification methods were impractical/inefficient and product yield was very low in all examples provided.

PCT Publication No. WO 2006/031725 to Pharmasset, Inc. describes the synthesis of 2'-C-substituted-2'-deoxy-2'-halo nucleosides via the nucleophilic ring opening of a 5-membered ring cyclic sulfate intermediate derived from 4,5-di-O-protected-2-methyl-2,3-dihydroxy-pentanoic acid with fluoride to produce a 2-methyl-2-fluoro 4,5-di-O-protected fluorinated acyclic sulfate ester compound. The fluorinated sulfate ester is treated with acid to deprotect the 4,5-hydroxyl groups and cyclized to 2'-fluoro-2'-C-methyl-γ-ribonolactone. The ribonolactone is then converted to the 2'-C-methyl-2'-deoxy-2'-halo nucleosides by reduction of the lactone and coupling with an appropriate base.

WO 2006/012440 to Pharmasset, Inc. describes the synthesis of 2'-C-substituted-2'-deoxy-2'-halo nucleosides via a 2'-fluoro-2'-C-substituted-γ-ribonolactone intermediate. The 2'-fluoro-2'-C-substituted-γ-ribonolactone is formed by cyclization of a 2-fluoro-4,5-di-O-protected-2,3-dihydroxypentanoic acid ethyl ester intermediate upon treatment with acid. The fluorination reaction is achieved by treating 4,5-di-O-protected-2-hydroxy-3-O-protected-pentanoic acid ethyl ester with DAST.

Otto et al. reported the synthesis and use of beta-2' or beta-3'-halonucleosides for the treatment of HIV, hepatitis B, and undesired cellular proliferation (U.S. Pat. No. 6,949,522). The syntheses disclosed produced 2',3'-dideoxy, 3',3'-dihalo nucleosides from glyceraldehyde or a sugar ring starting material; 2',3'-dideoxy, 3'-halo nucleosides from a lactol starting material; and 2',3'-dideoxy-2'-halo nucleosides from glyceraldehyde as a starting material that proceeds via a lactone intermediate that is selectively reduced to afford a 2',3'-hydro product.

Clark et al. disclosed the synthesis and antiviral activity of 2'-deoxy-2'-fluoro-2'-C-methylcytidine as an inhibitor of hepatitis C virus (Clark et al., *J. Med. Chem.* 2005, 48:5504-5508). Synthesis of the product compound proceeded through $N^4$-benzoyl-1-(2-methyl-3,5-di-O-benzoyl-β-D-arabinofuranosyl)cytosine as a key intermediate, which was oxidized to the corresponding 2'-ketone derivative by reaction with trifluoroacetic anhydride in DMSO under Swern oxidation conditions. The 2'-ketone derivative was reacted with methyllithium at −78° C. in diethyl ether to afford protected 1-[2-C-methyl-3,5-O-(tetraisopropyldisiloxane-1,3-diyl)1-β-D-arabinofuranosyl]cytosine, and the 3',5'-silyl protecting group was removed by reaction in TBAF/acetic acid. Clark et al. warn against the use of DAST for fluorination of tertiary alcohol groups because the reaction is substrate specific and stereochemically unpredictable.

Shi et al. reported the syntheses and antiviral activities of a series of D- and L-2'-deoxy-2'-fluororibonucleosides in a hepatitis C replicon system (Shi et al., *Bioorganic & Medicinal Chemistry* (2005), 13:1641-1652). The halo-substituted nucleosides tested had a single halo substituent at the 2'-position on the nucleoside sugar, and were prepared by direct conversion of D-2,2'-anhydrocytidine to (2'R)-D-2'-deoxy-2'-fluorocytidine by reaction with potassium fluoride and crown ether according to the method of Mengel and Guschlbauer (*Angew. Chem. Int. Ed. Engl.* 1978, 17:525).

There remains a need for discovering improved synthetic routes and new synthetic intermediates in the preparation of 2'-C-methyl-2'-halo-nucleoside analogue derivatives.

It is an object of the present invention to provide a stereochemically predictable and reliable process for the selective addition of alkyl and halo substituents at the 2'-C-position of a nucleoside analogue.

It is another object of the present invention to provide an efficient process that utilizes a minimum number of steps and a readily available, inexpensive starting material for preparing a key intermediate in the synthesis of a 2'-C-methyl-2'-halo-nucleoside analogue.

It is still another object of the present invention to provide a process that employs non-toxic reagents and provides the key intermediate in good percent product yield.

SUMMARY OF THE INVENTION

Historically, the addition of halogen atoms, particularly fluorine, has presented a challenge for researchers attempting to find a direct and simplified process for adding the atom to a precursor compound to provide a 2-deoxy-2-halo-2-C-substituted-D-ribono-1,4-lactone that then can be used in the synthesis of nucleoside analogue derivatives. In particular, the desired stereochemistry of the halogen and other substituents (typically alkyl) at the 2 position has been difficult to produce because of the competition between substitution with the halogen and elimination of the leaving group at the tertiary carbon to produce a byproduct with an exocyclic double bond. A process that allows nucleophilic substitution with a halogen atom to overtake elimination in this balance has been lacking. It now has been found that a halogen, and particularly a fluorine atom can be efficiently introduced at a tertiary center of an isopropylidene-arabinono-1,5-lactone to afford a 2-C-substituted-2-fluoro-ribonolactone using the process provided herein.

In one embodiment, it was surprisingly found that 2-deoxy-2-fluoro-2-C-substituted lactone compounds can be produced in high yields by nucleophilic displacement on 3,4-O-isopropylidene-2-C-substituted-D-arabinono-1,5-lactone or a halogenated derivative thereof using certain fluorinating reagents under anhydrous conditions.

In one embodiment, the invention provides a process of producing a 2-halo, and particularly 2-fluoro-2-C-substituted-1,5-lactone compound which includes:

a) providing a compound of structure (i) or (ii)

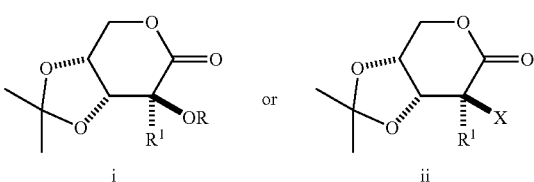

where OR is a suitable leaving group; $R^1$ is $C_{1-10}$ alkyl, $C_{1-4}$ lower alkyl, $C_{3-8}$ cycloalkyl, alkenyl including vinyl, alkynyl, including acetylene, alkenyl, $CF_3$, cyano, aryl, benzyl, or heterocycle; and X is a halogen atom;

b) contacting the compound with a fluorinating agent under anhydrous conditions.

In certain embodiments, the fluorinating agent is tris(dimethylamino)sulfonium difluorotrimethyl silicate (TASF).

In one embodiment, OR is a trifluoromethanesulfonate ester triflate). In another embodiment, OR is a methanesulfonate ester (mesylate). In yet another embodiment, OR is a p-toluenesulfonate ester (tosylate).

In certain embodiment, the reaction contains less than 1%, less than 0.1%, or less than 0.01% water.

In certain embodiments, the process produces a compound of Formula (II)

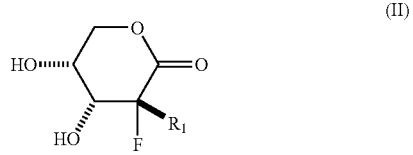

wherein $R^1$ is $C_{1-10}$ alkyl, $C_{1-4}$ lower alkyl, $C_{3-8}$ cycloalkyl, alkenyl including vinyl, alkynyl, including acetylene, alkenyl, $CF_3$, cyano, aryl, benzyl, or heterocycle, in at least 40% or more yield.

In certain subembodiments, the compound of Formula (II) is produced in at least 50%, at least 55%, at least 60%, at least 70% or at least 80% or more yield.

In one subembodiment, $R^1$ in the compound of Formula (II) is methyl. In another embodiment, $R^1$ is ethyl. In another embodiment, $R^1$ is vinyl. In yet another embodiment, $R^1$ is —C≡CR², wherein $R^2$ is $C_{1-10}$ alkyl, $C_{1-4}$ lower alkyl, $C_{3-8}$ cycloalkyl, $CF_3$, cyano, aryl, benzyl, or heterocycle. In another embodiment, $R^1$ cyano. In another embodiment, $R^1$ is benzyl. In yet another embodiment, $R^1$ is a heterocycle.

In one embodiment, the process further includes converting a compound of Formula (II) to a 1,4-lactone compound. In one embodiment, this conversion includes contacting the product from step (b) with an acid in a suitable organic solvent. In one embodiment, the acid is an organic acid. In one subembodiment, the acid is trifluoroacetic acid. In another subembodiment, the acid is acetic acid. In another embodiment, the acid is an aryl or alkyl sulfonic acid. In one subembodiment the solvent is 1,4-dioxane. In one embodiment, the 1,4-lactone product can be a 2-deoxy-2-halo-2-C-methyl-D-ribono-1,4-lactone of Formula (B):

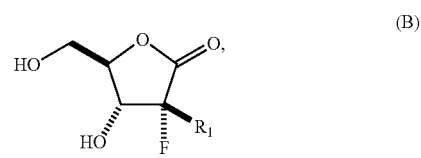

wherein $R^1$ is $C_{1-10}$ alkyl, $C_{1-4}$ lower alkyl, $C_{3-8}$ cycloalkyl, alkenyl including vinyl, alkynyl including acetylene, alkenyl, $CF_3$, cyano, aryl, benzyl, or heterocycle.

In certain embodiments, these compounds can be further modified by reduction of the lactone, derivitization of the resulting hydroxyl to a suitable leaving group and substitution with a base (including purine or pyrimidine bases) to provide a 2'-fluoro-2'-branched nucleoside including 2'-deoxy-2'-fluoro-2'-C-methyl-D-ribonofuranosyl nucleoside analogues.

DETAILED DESCRIPTION OF THE INVENTION

The present invention provides a process for preparing a compound of Formula (I) and Formula (II), which are a key intermediates in the synthesis of certain nucleoside analogues, including 2'-branched nucleoside analogs.

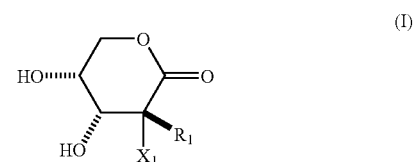

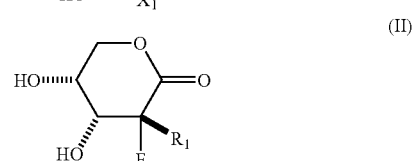

wherein $R^1$ is $C_{1-10}$ alkyl, $C_{1-4}$ lower alkyl, $C_{3-8}$ cycloalkyl, alkenyl including vinyl, alkynyl including acetylene, alkenyl, $CF_3$, cyano, aryl, benzyl, or heterocycle; and $X_1$ is halogen.

In one embodiment, the present invention further provides a process for preparing compounds of Formula (A) and Formula (B), which are key intermediates in the synthesis of certain nucleoside analogues, including 2'-branched nucleoside analogs.

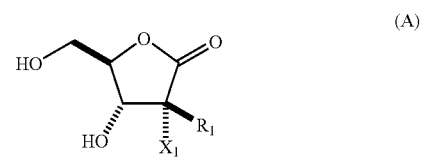

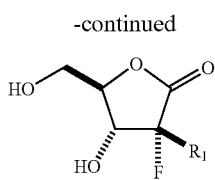

(B)

wherein R¹ is $C_{1-10}$ alkyl, $C_{1-4}$ lower alkyl, $C_{3-8}$ cycloalkyl, alkenyl including vinyl, alkynyl including acetylene, alkenyl, $CF_3$, cyano, aryl, benzyl, or heterocycle and $X_1$ is halogen.

DEFINITIONS

Whenever a range is referred to within the specification, such as $C_{1-10}$ alkyl, the range independently refers to each element. For example, $C_{1-10}$ alkyl refers independently to $C_1$-alkyl, $C_2$-alkyl, $C_3$-alkyl, $C_4$-alkyl, $C_5$-alkyl, $C_6$-alkyl, $C_7$-alkyl, $C_8$-alkyl, $C_9$-alkyl and $C_{10}$-alkyl.

The term alkyl, as used herein, unless otherwise specified, includes a saturated straight, branched, or cyclic hydrocarbon, including but not limited to those of $C_1$ to $C_{10}$, and preferably $C_1$-$C_4$, including methyl, ethyl, propyl, isopropyl, cyclopropyl, methylcyclopropyl, butyl, isobutyl, t-butyl, sec-butyl, cyclobutyl, and (cyclopropyl)methyl. Cycloalkyl groups include groups with 3 to 10 carbons. The alkyl group specifically includes fluorinated alkyls such as $CF_3$ and other halogenated alkyls such as $CH_2CF_2$, $CF_2CF_3$, the chloro analogs, and the like.

The term alkenyl, as used herein, unless otherwise specified, includes a $C_2$ to $C_{10}$ hydrocarbon with at least one double bond, including but not limited to vinyl.

The term alkynyl, as used herein, unless otherwise specified, includes a $C_2$ to $C_{10}$ hydrocarbon with at least one triple bond, including but not limited to acetylene.

The term alkenyl, as used herein, unless otherwise specified, includes a $C_3$ to $C_{10}$ hydrocarbon with at least two double bonds that share a central carbon atom.

The alkyl, alkenyl and alkynyl groups can be optionally substituted with one or more moieties selected from the group consisting of aryl, heteroaryl, heterocyclic, carbocycle, alkoxy, heterocyclooxy, heterocycloalkoxy, aryloxy, arylalkoxy, heteroaryloxy; heteroarylalkoxy, carbohydrate, amino acid, amino acid esters, amino acid amides, alditol, halo, haloalkyl, hydroxyl, carboxyl, acyl, acyloxy, amino, amido, alkylamino, dialkylamino, arylamino, nitro, cyano, thiol, imide, sulfonic acid, sulfate, sulfonyl, sulfanyl, sulfinyl, sulfamoyl, carboxylic ester, carboxylic acid, amide, phosphonyl, phosphinyl, phosphoryl, thioester, thioether, oxime, hydrazine, carbamate, phosphonic acid, phosphate, phosphonate, phosphinate, sulfonamido, carboxamido, hydroxamic acid, sulfonylimide, substituted or unsubstituted urea connected through nitrogen including but not limited to $NHCONH_2$ and NHCONHR; or any other desired functional group that does not inhibit the pharmacological activity of this compound, either unprotected, or protected as necessary, as known to those skilled in the art, for example, as taught in Greene, et al., Protective Groups in Organic Synthesis, John Wiley and Sons, Second Edition, 1991, hereby incorporated by reference.

The term aryl, as used herein, and unless otherwise specified, includes phenyl, biphenyl, or naphthyl, and preferably phenyl. The term aryl includes heteroaryl groups. The aryl group can be optionally substituted with one or more of the moieties selected from the group consisting of alkyl, heteroaryl, heterocyclic, carbocycle, alkoxy, aryloxy, aryloxy, arylalkoxy, heteroaryloxy; heteroarylalkoxy, carbohydrate, amino acid, amino acid esters, amino acid amides, alditol, halo, haloalkyl, hydroxyl, carboxyl, acyl, acyloxy, amino, amido, alkylamino, dialkylamino, arylamino, nitro, cyano, thiol, imide, sulfonic acid, sulfate, sulfonyl, sulfanyl, sulfinyl, sulfamoyl, carboxylic ester, carboxylic acid, amide, phosphonyl, phosphinyl, phosphoryl, thioester, thioether, oxime, hydrazine, carbamate, phosphonic acid, phosphate, phosphonate, phosphinate, sulfonamido, carboxamido, hydroxamic acid, sulfonylimide or any other desired functional group that does not inhibit the pharmacological activity of this compound, either unprotected, or protected as necessary, as known to those skilled in the art, for example, as taught in Greene, et al., "Protective Groups in Organic Synthesis," John Wiley and Sons, Second Edition, 1991. Alternatively, adjacent groups on the aryl ring may combine to form a 5 to 7 membered carbocyclic, aryl, heteroaryl or heterocylic ring. In another embodiment, the aryl ring is substituted with an optionally substituted cycloalkyl (such as cyclopentyl or cyclohexyl), or an alkylene dioxy moiety (for example methylenedioxy).

The term heterocyclic or heterocycle includes nonaromatic cyclic groups that may be partially (contains at least one double bond) or fully saturated and wherein there is at least one heteroatom, such as oxygen, sulfur, nitrogen, or phosphorus in the ring. The term heteroaryl or heteroaromatic, as used herein, includes aromatic groups that include at least one sulfur, oxygen, nitrogen or phosphorus in the aromatic ring. Nonlimiting examples of heterocylics and heteroaromatics are pyrrolidinyl, tetrahydrofuryl, piperazinyl, piperidinyl, morpholino, thiomorpholino, tetrahydropyranyl, imidazolyl, pyrrolinyl, pyrazolinyl, indolinyl, dioxolanyl, or 1,4-dioxanyl. aziridinyl, furyl, furanyl, pyridyl, pyrimidinyl, benzoxazolyl, 1,2,4-oxadiazolyl, 1,3,4-oxadiazolyl, 1,3,4-thiadiazole, indazolyl, 1,3,5-triazinyl, thienyl, isothiazolyl, imidazolyl, tetrazolyl, pyrazinyl, benzofuranyl, quinolyl, isoquinolyl, benzothienyl, isobenzofuryl, pyrazolyl, indolyl, isoindolyl, benzimidazolyl, purinyl, carbazolyl, oxazolyl, thiazolyl, benzothiazolyl, isothiazolyl, 1,2,4-thiadiazolyl, isooxazolyl, pyrrolyl, quinazolinyl, cinnolinyl, phthalazinyl, xanthinyl, hypoxanthinyl, pyrazole, imidazole, 1,2,3-triazole, 1,2,4-triazole, 1,2,3-oxadiazole, thiazine, pyridazine, or pteridinyl, wherein said heteroaryl or heterocyclic group can be optionally substituted with one or more substituent selected from the same substituents as set out above for aryl groups. Functional oxygen and nitrogen groups on the heteroaryl group can be protected as necessary or desired. Suitable protecting groups can include trimethylsilyl, dimethylhexylsilyl, t-butyldimethylsilyl, and t-butyldiphenylsilyl, trityl or substituted trityl, alkyl groups, acyl groups such as acetyl and propionyl, methanesulfonyl, and p-toluenesulfonyl.

The term aralkyl, as used herein, and unless otherwise specified, refers to an aryl group as defined above linked to the molecule through an alkyl group as defined above. The aryl and alkyl portions can be optionally substituted as described above.

The term halo or halogen, as used herein, includes chloro, bromo, iodo and fluoro.

The term acyl, as used herein, refers to a group of the Formula C(O)R', wherein R' is an alkyl, aryl, alkaryl or aralkyl group, or substituted alkyl, aryl, aralkyl or alkaryl, wherein these groups are as defined above.

The term purine or pyrimidine base includes, but is not limited to, adenine, $N^6$-alkylpurines, $N^6$-acylpurines (wherein acyl is C(O)(alkyl, aryl, alkylaryl, or arylalkyl), $N^6$-benzylpurine, $N^6$-halopurine, $N^6$-vinylpurine, $N^6$-acetylenic purine, $N^6$-acyl purine, $N^6$-hydroxyalkyl purine, $N^6$-thioalkyl purine, $N^2$-alkylpurines, $N^2$-alkyl-6-thiopurines, thymine, cytosine, 5-fluorocytosine, 5-methylcytosine, 6-azapyrimidine, including 6-azacytosine, 2- and/or 4-mercaptopyridine, uracil, 5-halouracil, including 5-fluorouracil, $C^5$-alkylpyrimidines, $C^5$-benzylpyrimidines, $C^5$-halopyrimidines, $C^5$-vinylpyrimidine, $C^5$-acetylenic pyrimidine, $C^5$-acyl pyrimidine, $C^5$-hydroxyalkyl purine, $C^5$-amidopyrimidine, $C^5$-cyanopyrimidine, $C^5$-nitropyrimidine, $C^5$-aminopyrimidine, $N^2$-alkylpurines, $N^2$-alkyl-6-thiopurines, 5-azacytidinyl, 5-azauracilyl, triazolopyridinyl, imidazolopyridinyl, pyrrolopyrimidinyl, and pyrazolopyrimidinyl. Purine bases include, but are not limited to, guanine, adenine, hypoxanthine, 2,6-diaminopurine, and 6-chloropurine. Functional oxygen and nitrogen groups on the base can be protected as necessary or desired. Suitable protecting groups are well known to those skilled in the art, and include trimethylsilyl, dimethylhexylsilyl, t-butyldimethylsilyl, and t-butyldiphenylsilyl, trityl, alkyl groups, and acyl groups such as acetyl and propionyl, methanesulfonyl, and p-toluenesulfonyl.

The term "protected" as used herein and unless otherwise defined refers to a group that is added to an oxygen, nitrogen, sulfur or phosphorus atom to prevent its further reaction or for other purposes. A wide variety of oxygen and nitrogen protecting groups are known to those skilled in the art of organic synthesis.

In one embodiment, the invention provides a process of producing a 2-fluoro-2-C-substituted-1,5-lactone compound of Formula (II) which includes:

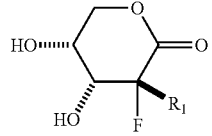

(II)

a) providing a compound of structure (i) or (ii)

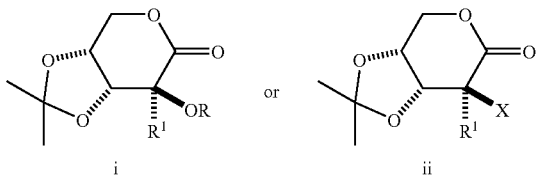

where OR is a suitable leaving group and X halogen; and

Wherein $R^1$ is $C_{1-10}$ alkyl, $C_{1-4}$ lower alkyl, $C_{3-8}$ cycloalkyl, alkenyl including vinyl, alkynyl including acetylene, alkenyl, $CF_3$, cyano, aryl, aralkyl including benzyl, or heterocycle; and b) contacting the compound with a fluorinating agent under conditions that allow replacement of the leaving group with a fluorine atom.

Leaving groups OR include but are not limited to arylsulfonate, including p-toluenesulfonate (tosylate), alkylsulfonate including methanesulfonate (mesylate), trifluoromethanesulfonate (triflate), allylsulfonate, 4-nitrobenzenesulfonate (nosylate), 4-bromobenzenesulfonate (brosylate), acetate, trifluoroacetate, arylsulfate, or alkylsulfate.

In preferred embodiments, step (b) is carried out under anhydrous conditions. Anhydrous as used herein refers to the substantial absence of water, which is achieved, e.g., by conducting the reaction under an inert gas and using substantially dry reagents, for example with less than 1% or less than 0.1% water.

In one particular embodiment, the fluorinating agent is tris(dimethylamino)sulfonium difluorotrimethyl silicate (TASF).

Other, less preferred nucleophilic fluorinating agents include but are not limited to HF, HF-amine complexes, including HF-pyridine, sulfur tetrafluoride, KF, KF/crown ether, CaF, LiF, NaF, silver(I) fluoride, CsF, antimony (III) fluoride, antimony (V) fluoride, n-Bu$_4$NF, cyanuric fluoride, tetrabutylammonium difluorotriphenylstannate, (diethylamino)sulfur trifluoride (DAST), morpholinosulfur trifluoride (Morpho-DAST), N,N-diethyl-1,1,2,3,3,3-hexafluororopropylamine, N,N-diethyl-1,2,3,3,3-pentafluororopropenamine, N,N-diethyl(2-chloro-1,1,2-trifluoroethyl)-amine and tetrabutylammonium difluorotriphenyl stannate. Chlorinating agents include but are not limited to HCl, chloride salts, thionyl chloride, PCl$_3$, and PCl$_5$. Brominating agents include but are not limited to HBr, bromide salts, thionyl bromide, PBr$_3$, and PBr$_5$. Iodinating agents include but are not limited to HI and iodide salts. TASF is a preferred fluorinating agent because of the optimized yield of the desired product.

Substitution of the leaving groups OR or X with halogen may be achieved with any nucleophilic halogenating agents known to those skilled in the art, however, TASF is a preferred halogenating agent because of the optimized yield of the desired product.

In certain embodiments, the process produces a compound of Formula (II)

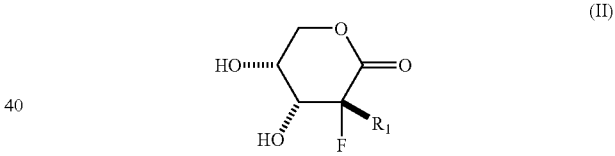

(II)

wherein $R^1$ $C_{1-10}$ alkyl, $C_{1-4}$ lower alkyl, $C_{3-8}$ cycloalkyl, alkenyl including vinyl, alkynyl including acetylene, alkenyl, $CF_3$, cyano, aryl, aralkyl including benzyl, or heterocycle, in at least 40% or more yield. In certain subembodiments, the compound of Formula (II) is produced in at least 50%, at least 55%, at least 60%, at least 70% or at least 80% or more yield.

In one subembodiment, $R^1$ in the compound of Formula (II) is methyl. In another subembodiment, $R^1$ is ethyl. In another subembodiment, $R^1$ is vinyl. In yet another subembodiment, $R^1$ is $-C\equiv CR^2$, wherein $R^2$ is $C_{1-10}$ alkyl, $C_{1-4}$ lower alkyl, $C_{3-8}$ cycloalkyl, $CF_3$, cyano, aryl, benzyl, or heterocycle. In another subembodiment, $R^1$ is $-C\equiv CH$.

In one embodiment, the process further includes converting a compound of Formula (II) to a 1,4-lactone compound. In one embodiment, this conversion includes contacting the product from step (b) with a suitable acid. In one embodiment, the acid is an organic acid. Suitable acids include but are not limited to trifluoroacetic acid, trichloroacetic acid, acetic acid, methylsulfonic acid, p-toluenesulfonic acid, and trifluoromethylsulfonic acid. In one subembodiment, the acid is trifluoroacetic acid. In another embodiment, the acid is methanesulfonic acid. In yet another embodiment, the acid is trichloroacetic acid. In one embodiment, the solvent is 1,4- dioxane. The 1,4-lactone product can be a 2-deoxy-2-fluoro-2-C-methyl-D-ribono-1,4-lactone a compound of Formula (B):

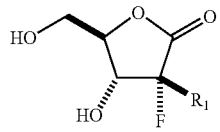
(B)

wherein $R^1$ is $C_{1-10}$ alkyl, $C_{1-4}$ lower alkyl, $C_{3-8}$ cycloalkyl, alkenyl including vinyl, alkynyl including acetylene, alkenyl, $CF_3$, cyano, aryl, aralkyl including benzyl, or heterocycle.

In certain embodiments, these compounds can be further modified by reduction of the lactone, derivitization of the resulting hydroxyl and addition of a base (including purine or pyrimidine bases) to provide a 2'-fluoro-2'-branched nucleoside including 2'-deoxy-2'-fluoro-2'-C-methyl-D-ribonofuranosyl nucleoside analogues.

In one embodiment, the process of Scheme I is provided:

SCHEME I

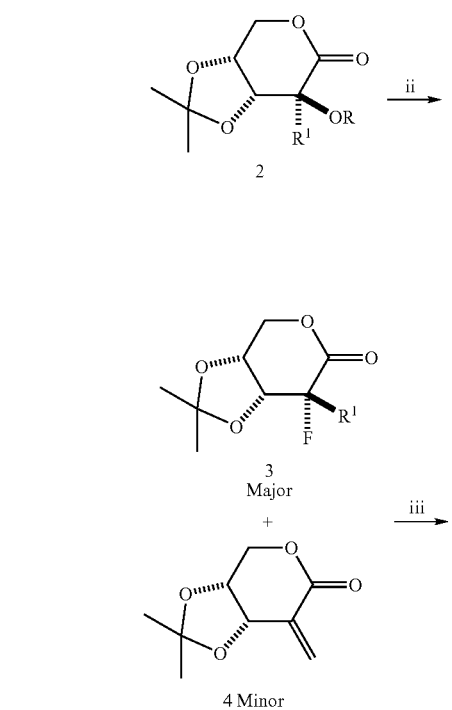

-continued

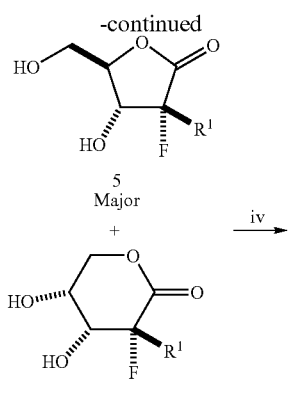

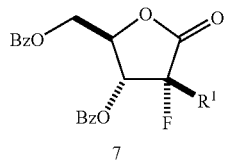

wherein OR is arylsulfonate, including p-toluenesulfonate (tosylate), alkylsulfonate including methanesulfonate (mesylate), trifluoromethanesulfonate (triflate), allylsulfonate, 4-nitrobenzenesulfonate (nosylate), 4-bromobenzenesulfonate (brosylate), acetate, trifluoroacetate, arylsulfate, or alkylsulfate; and $R^1$ is $C_{1-10}$ alkyl, $C_{1-4}$ lower alkyl, $C_{3-8}$ cycloalkyl, alkenyl including vinyl, alkynyl, including acetylene, alkenyl, $CF_3$, cyano, aryl, benzyl, or heterocycle.

In a subembodiment, OR is triflate and $R^1$ is lower alkyl. In another subembodiment, $R^1$ is methyl. In still another subembodiment, OR is mesylate. In another subembodiment, OR is triflate and $R^1$ is acetylene. In yet another subembodiment OR is triflate and $R^1$ is vinyl.

In another embodiment, the process of Scheme II is provided:

SCHEME II

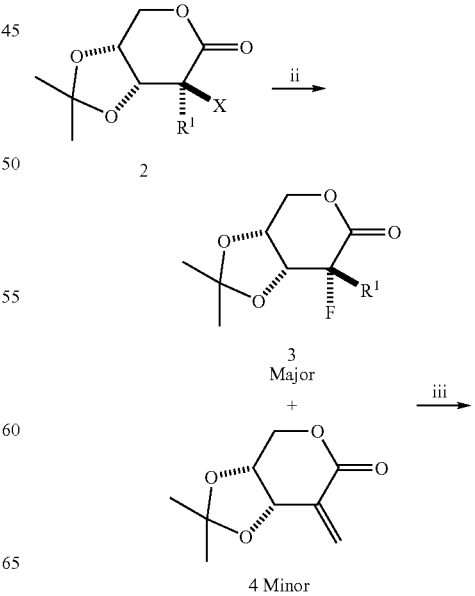

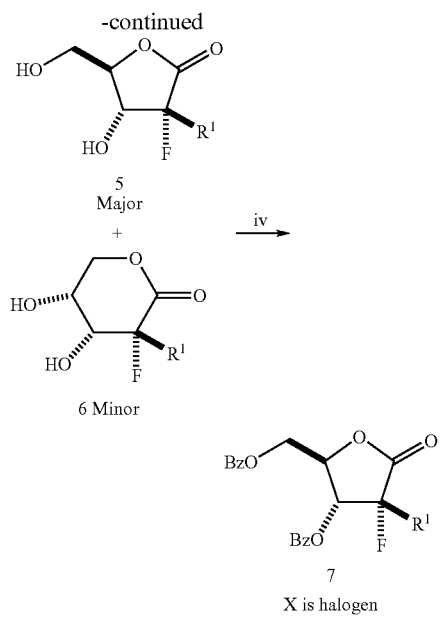

wherein X is chloro, bromo, iodo or fluoro. The stereochemistry at the 2-position of the lactone is inverted as the result of the displacement of the halogen group by fluoride; and $R^1$ is $C_{1-10}$ alkyl, $C_{1-4}$ lower alkyl, $C_{3-8}$ cycloalkyl, alkenyl including vinyl, alkynyl, including acetylene, alkenyl, $CF_3$, cyano, aryl, benzyl, or heterocycle.

In a subembodiment, X is chloro and $R^1$ is methyl. In another subembodiment, X is bromo and $R^1$ is methyl. In another subembodiment, X is chloro or bromo and $R^1$ is acetylene. In yet another subembodiment, X is chloro or bromo and $R^1$ is vinyl.

In one embodiment, the process of Scheme IIIA is provided:

SCHEME IIIA

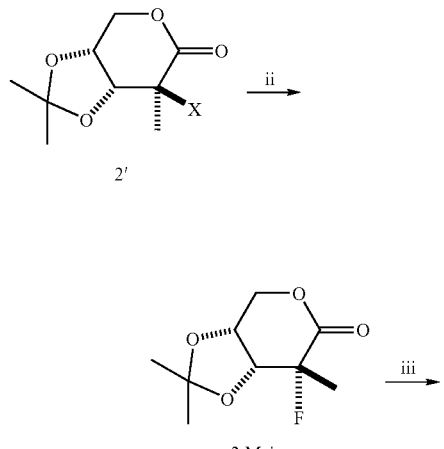

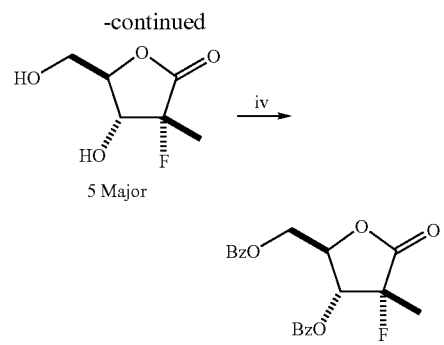

wherein OR is arylsulfonate, including p-toluenesulfonate (tosylate), alkylsulfonate including methanesulfonate (mesylate), trifluoromethanesulfonate (triflate), allylsulfonate, 4-nitrobenzenesulfonate (nosylate), 4-bromobenzenesulfonate (brosylate), acetate, trifluoroacetate, arylsulfate, or alkylsulfate.

In another embodiment, the process of Scheme IIIB is provided:

SCHEME IIIB

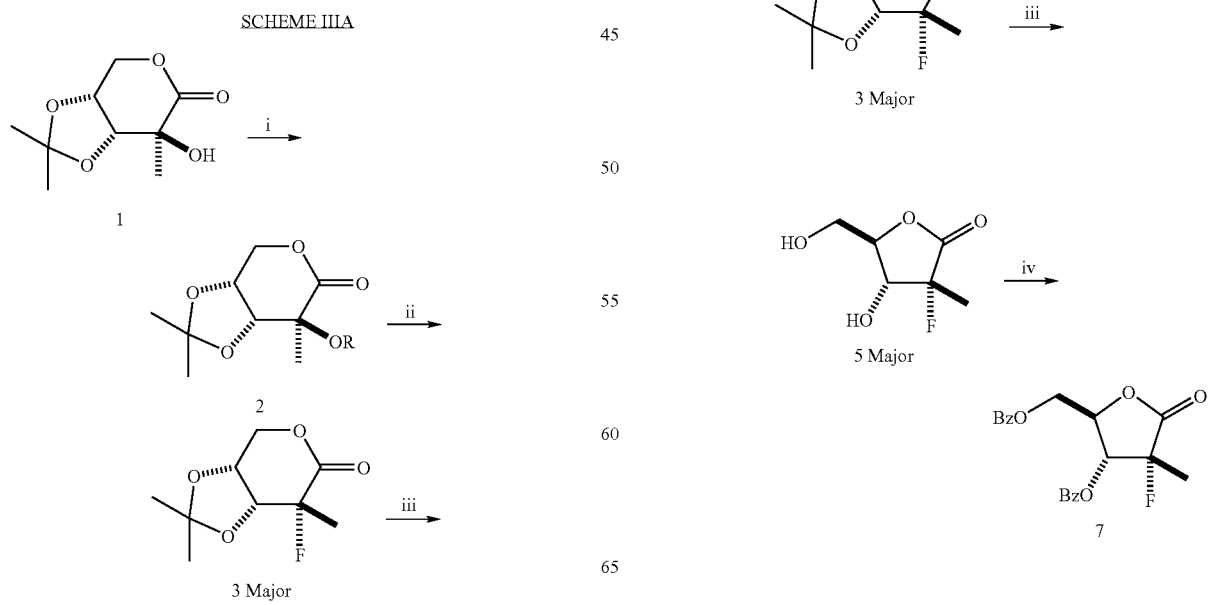

wherein X is halogen.

In one specific embodiment, the process of Scheme IV is provided:

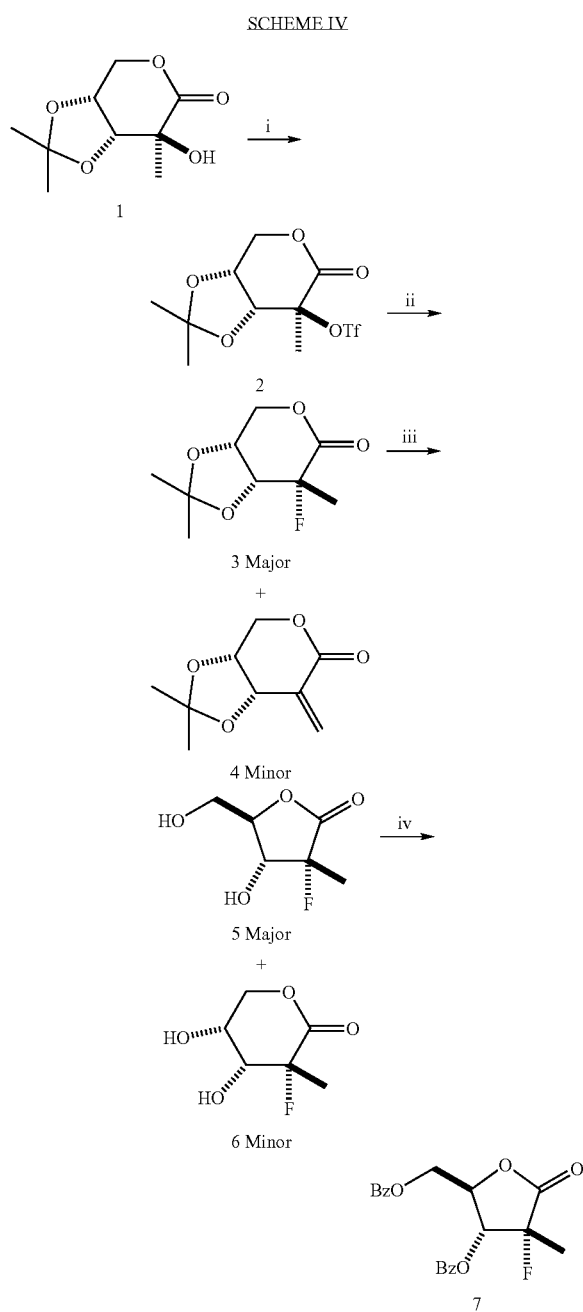

wherein OTf is triflate.

In any of the above schemes, in one embodiment steps i and ii and are carried out under anhydrous conditions. In certain embodiments, the reagents are all anhydrous, including all starting materials and solvents. The introduction of the fluoro atom to the 1,5-lactone is achieved stereospecifically with inversion at the carbon. The stereochemistry of the desired product is controlled by the stereochemistry of the starting lactone.

The use of tris(dimethylamino)sulfonium difluorotrimethyl silicate (TASF) as the fluorinating agent in specific amounts of equivalents and in a specific method of addition to the reaction mixture, i.e., lack of exposure to atmospheric conditions due to the hygroscopic nature of TASF, results in the formation of 2-fluoro-3,4-O-isopropylidene-2-C-methyl-D-ribono-1,5-lactone as the major product, rather than the elimination byproduct 4. The 2-fluoro-3,4-O-isopropylidene-2-C-methyl-D-ribono-1,5-lactone then can be converted to 2-deoxy-2-halo-2-C-methyl-D-ribono-1,4-lactone as a major product by treatment with acid. 2-deoxy-2-halo-2-C-methyl-D-ribono-1,5-lactone is formed as a minor byproduct.

Step i:

Often hydroxy groups on a reactant molecule can be prevented from participating in a reaction by using protecting groups known to those of skill in the art and as taught, for example, by Greene and Wuts, *Protective Groups in Organic Synthesis* (1999), Third Ed., John Wiley & Sons, Inc., New York, N.Y. Common hydroxy-protecting groups include ethers, esters, particularly benzoyl groups.

In one embodiment, the 2-OH group of a 3,4-O-isopropylidene-2-C-methyl-D-arabinono-1,5-lactone is converted to an leaving group to facilitate substitution with a halogen atom. In one embodiment, the preparation of the 2-OR leaving group is formed under anhydrous conditions. The temperature can be reduced to below 0° C., in certain embodiments to below −10° C., below −20° C., below −30° C. or below −40° C.

In one embodiment, the leaving group OR is arylsulfonate, including p-toluenesulfonate (tosylate), alkylsulfonate including methanesulfonate (mesylate), trifluoromethanesulfonate (triflate), allylsulfonate, 4-nitrobenzenesulfonate (nosylate), 4-bromobenzenesulfonate (brosylate), acetate, trifluoroacetate, arylsulfate, or alkylsulfate. Starting compounds for the synthesis of this invention can be obtained commercially. For example, 3,4-O-isopropylidene-2-C-methyl-D-arabinono-1,5-lactone, is obtainable commercially from a company such as Prime Organics Ltd. Other compounds that can be used as starting materials for this process include protected 2-C-methyl-D-arabinono-1,4-lactone.

Step ii:

In certain embodiments, a halogen substituted compound is used as starting material and is commercially obtained. In these instances, a separate step to include a leaving group (i.e. step i) is not required.

The 2-C-methyl-1,5-lactone product of step i or a commercially available 2-C-methyl-2-halogenated-1,5-lactone is reacted with a fluorinating agent, under conditions that allow substitution of the leaving group. This reaction is typically carried out under anhydrous conditions. In one embodiment, the reaction contains less than 1%, less than 0.1%, or less than 0.01% water.

In one embodiment, the fluorinating agent is tris(dimethylamino)sulfonium difluorotrimethyl silicate (TASF). Other, less preferred fluorinating agents include but are not limited to HF, HF-amine complexes, including HF-pyridine, sulfur tetrafluoride, KF, KF/crown ether, CaF, LiF, NaF, silver(I) fluoride, CsF, antimony (III) fluoride, antimony (V) fluoride, n-Bu₄NF, cyanuric fluoride, tetrabutylammonium difluorotriphenylstannate, (diethylamino)sulfur trifluoride (DAST), morpholinosulfur trifluoride (Morpho-DAST), N,N-diethyl-1,1,2,3,3,3-hexafluororopropylamine, N,N-diethyl-1,2,3,3,3-pentafluororopropenamine, N,N-diethyl(2-chloro-1,1,2-trifluoroethyl)-amine and tetrabutylammonium difluorotriphenyl stannate.

Suitable solvents include dichloromethane, toluene, tetrahydrofuran, 1,4-dioxane, ethyl ether, acetonitrile, tert-butylmethyl ether (TBME), 2-methyl THF, dichloroethane, chloroform, isopropyl ether, xylenes, dimethoxy ethane, diethoxy methane.

This reaction is typically carried out at about equal to or less than 0° C., typically at less than −2° C., about −5° C., less than −5° C., about −10° C., or less. In one embodiment, the halogenating agent is added after conversion of an arabino-1,5-lactone to a ribono-1,5-lactone. In one embodiment, the temperature is increased to about 0° C. after contact with the halogenating agent. The substitution reaction is stereospecific, occurring with inversion at the carbon.

Step iii:

A 2-halo-2-C-substituted-D-ribono-1,5-lactone can be converted to 2-deoxy-2-halo-2-C-substituted-D-ribono-1,4-lactone by contacting the compound with an acid. The reaction produces a mixture of 1,4-lactone as the major product, with a 2-halo-3,4-O-isopropylidene-2-C-substituted-D-ribono-1,5-lactone as the minor product. This reaction can be conducted at room temperature.

In one embodiment, the acid is an organic acid. Suitable acids include but are not limited to trifluoroacetic acid, trichloroacetic acid, acetic acid, methylsulfonic acid, p-toluenesulfonic acid, and trifluoromethylsulfonic acid. In one embodiment, the acid is an organic acid. In one subembodiment, the acid is trifluoroacetic acid.

In certain embodiments, the deprotection is carried out for longer time periods and additional acid is added to maximize the formation of product. For example, in one embodiment, to provide the 1,4-lactone intermediate in greatest yields, deprotection reaction time can be increased from what was previously used. In addition, additional TFA (trifluoroacetic acid)/ $H_2O$/dioxane can be added, and the acetone byproduct can be removed by vacuum distillation to drive the reaction over its equilibrium point.

Step iv:

The 2-deoxy-2-fluoro-2-C-methyl-D-ribono-1,4-lactone can be used in a continuous synthesis to form a fluoro-containing nucleoside analogue. Hydroxy groups on a reactant molecule can be blocked from participating in a reaction by using protecting groups known to those of skill in the art and as taught, for example, by Greene and Wuts, *Protective Groups in Organic Synthesis* (1999), Third Ed., John Wiley & Sons, Inc., New York, N.Y. Common hydroxy-protecting groups include ethers, esters, and particularly benzoyl groups. Benzoyl chloride can easily and effectively be added to a ribonolactone intermediate in the presence of a base, to provide a 3,5-di-benzoyl protected ribonolactone.

In one embodiment, the steps for protection include: dissolving 2-deoxy-2-fluoro-2-C-methyl-D-ribono-1,4-lactone in pyridine and cooling the resulting solution to about 0° C. under an inert atmosphere, including an argon or nitrogen atmosphere, adding benzoyl chloride dropwise over a short time, and then bringing the resulting solution to room temperature and stirring for about 3-5 hours. Additional benzoyl chloride then is added and the solution stirred for about 15-20 hours, after which a further amount of benzoyl chloride is added. The solution is stirred about another 2-4 hours, a final portion of benzoyl chloride added, and the solution was aged for about another hour. The reaction is then quenched by the addition of water, and the solids formed during the reaction are dissolved. After stirring the solution for about 5 minutes, crystals precipitate from the solution. The crystals are filtered and washed with water. The resulting solid is dissolved in dichloromethane and washed with an HCl solution. The organic layer produced from the dichloromethane/HCl treatment is dried, filtered and concentrated in vacuo to afford an off-white residue. The residue is purified by flash chromatography to provide 3,5-dibenzoyl-2-deoxy-2-fluoro-2-C-methyl-D-ribono-1,4-lactone.

In an alternate embodiment, a process is provided for preparing a compound of Formula (I), which is a key intermediate in the synthesis of certain nucleoside analogues, including 2'-branched nucleoside analogs.

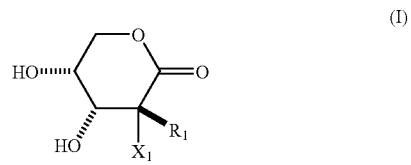

(I)

wherein $R^1$ is $C_{1-10}$ alkyl, $C_{1-4}$ lower alkyl, $C_{3-8}$ cycloalkyl, alkenyl including vinyl, alkynyl including acetylene, alkenyl, $CF_3$, cyano, aryl, aralkyl including benzyl, or heterocycle; and $X_1$ is halogen.

In one embodiment, the present invention further provides a process for preparing a compound of Formula (A), which is a key intermediate in the synthesis of certain nucleoside analogues, including 2'-branched nucleoside analogs.

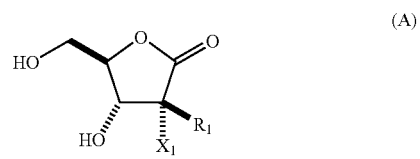

(A)

wherein $R^1$ and $X_1$ are as defined above.

Identity of all product compounds described below was confirmed by extensive NMR, MS, IR, optical rotation $\alpha\text{-}_D$, melting point, CHN elemental analysis, and/or crystal structure determinations.

EXAMPLES

Example 1

3,4-O-Isopropylidene-2-C-methyl-2-O-trifluoromethanesulfonyl-D-arabinono-1,5-lactone

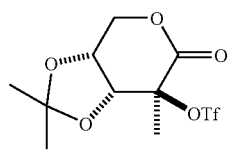

3,4-O-Isopropylidene-2-C-methyl-D-arabinono-1,5-lactone (7.09 g, 0.035 mol) was dissolved in anhydrous dichloromethane (110 ml). Anhydrous pyridine was added (25.5 ml, 0.315 mol) to the solution, which was then cooled to −40° C. under an argon atmosphere. Trifluoromethanesulfonic anhydride (28.4 ml, 0.168 mol) or triflate was added dropwise over 0.5 h. The mixture was allowed to warm slowly to −10° C. over 3.5 h, after which time the color became deep red and t.l.c. (ethyl acetate/heptane, 1:2) indicated conversion of starting material ($R_f$ 0.33) to a major product ($R_f$ 0.55). The reaction mixture was diluted with dichloromethane (500 ml)

and washed with 1M HCl$_{aq}$ (280 ml). The aqueous layer was extracted with dichloromethane (200 ml×2) and the combined organic layers were washed with brine (400 ml), dried (magnesium sulfate), filtered and concentrated in vacuo. The crude red/brown triflate (9.5 g) was purified by flash column chromatography (loaded from dichloromethane, eluted with heptane then ethyl acetate/heptane, 1:5) to give 3,4-O-isopropylidene-2-C-methyl-2-O-trifluoromethanesulfonyl-D-arabinono-1,5-lactone (5.51 g, 47%) as a white solid.

Data for $C_{10}H_{13}F_3O_7S$ 334.27 gmol$^{-1}$; $R_f$=0.33, ethyl acetate/heptane, 1:5; $^1$H NMR $\delta_H$ (400 MHz, CDCl$_3$): 1.37, 1.44 (6H, 2×s, C(CH$_3$)$_2$), 1.98 (3H, s, CH$_3$), 4.55 (1H, a-d, $J_{5,5'}$ 13.0, H-5), 4.62 (1H, a-d, J 7.2, H-4), 4.70 (1H, a-d, J 9.2, H-3), 4.76 (1H, dd, $J_{5,5'}$ 13.0, $J_{5,4}$ 1.7, H-5').

Example 2

2-Deoxy-2-fluoro-3,4-O-isopropylidene-2-C-methyl-D-ribono-1,5-lactone

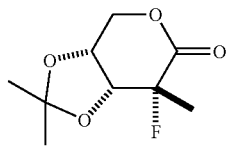

3,4-O-isopropylidene-2-C-methyl-2-O-trifluoromethanesulfonyl-D-arabinono-1,5-lactone (5.48 g, 0.0164 mol) was dissolved in anhydrous dichloromethane (56 ml) giving a pale yellow solution which was cooled to −5° C. under an argon atmosphere. Tris(dimethylamino)sulfur trimethylsilyl difluoride, TASF, (3×5 g, 0.0538 mol) was added to the solution directly from the bottles due to its very hygroscopic nature. The solution was stirred at 0° C. for 5 min then allowed to warm to room temperature for 1 h. T.l.c. (ethyl acetate/heptane, 1:1) indicated complete conversion of the starting material ($R_f$ 0.72) to a major, but faint product ($R_f$ 0.30). The reaction mixture was diluted with dichloromethane (420 ml) and washed with water (220 ml×2). The organic layer was dried (magnesium sulfate), filtered and concentrated in vacuo. The crude brown residue (4.4 g) was purified by flash column chromatography (loaded from dichloromethane, eluted with heptane then ethyl acetate/heptane, 1:2) to give 2-deoxy-2-fluoro-3,4-O-isopropylidene-2-C-methyl-D-ribono-1,5-lactone (1.36 g, 42%) as a white solid.

Data for $C_9H_{13}FO_4$ 204.20 gmol$^{-1}$; $R_f$=0.30, ethyl acetate/heptane, 1:1; $^1$H NMR $\delta_H$ (400 MHz, CDCl$_3$): 1.34, 1.51 (6H, 2×s, C(CH$_3$)$_2$), 1.66 (3H, d, $J_{H,F}$ 22.5, CH$_3$), 4.39 (1H, dd, $J_{5,5'}$ 13.3, $J_{5,4}$ 2.4, H-5), 4.48 (1H, dd, $J_{5',5}$ 13.3, $J_{5',4}$ 0.9, H-5'), 4.56-4.61 (2H, m, H-3, H-4); $^{13}$C NMR $\delta_C$ (100 MHz, CDCl$_3$): 19.46 (d, $^2J_{C,F}$ 26.1, CH$_3$), 24.62, 26.31 (C(CH$_3$)$_2$), 68.93 (C-5), 71.84 (d, $^3J_{C,F}$ 4.6, C-4), 78.18 (d, $^2J_{C,F}$ 16.8, C-3), 89.82 (d, $^1J_{C,F}$ 192.5, C-2), 111.49 (C(CH$_3$)$_2$), 168.1 (d, $^2J_{C,F}$ 25.1, C=O); $^{19}$F NMR $\delta_F$ (376 MHz, CDCl$_3$): −159.80 (1F, m, $^3J_{F,H}$ 22.9, F). NMR assignments confirmed using COSY and HMQC experiments; Mass Spec m/z (APCI-): 203.3 ([M−H]$^-$, 50%), 236.3 (100%).

Example 3

Data for 2-deoxy-2-fluoro-2-C-methyl-D-ribono-1,5-lactone

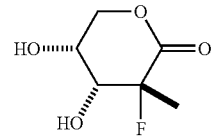

($C_6H_9FO_4$) 164.13 gmol$^{-1}$; $R_f$=0.45, ethyl acetate/heptane, 8:1; m.p.: 119-120° C. then 133-135° C.[1]; $[\alpha]_D^{20}$: +115.025 (c, 0.9284 in CH$_3$CN); $\nu_{max}$ (KBr disc): 3414 cm$^{-1}$, 3276 cm$^{-1}$ (O—H), 1778 cm$^{-1}$ (C=O); $^1$H NMR $\delta_H$ (400 MHz, CD$_3$CN): 1.57 (3H, d, $J_{H,F}$ 23.7, CH$_3$), 2.19 (1H, br-s, OH), 4.04 (1H, dd, $^3J_{H,F}$ 22.5, $J_{3,4}$ 7.6, H-3), 4.12 (1H, br-s, OH), 4.54 (1H, dd, $J_{5,5'}$ 12.4, $J_{5,4}$ 6.3, H-5), 4.61 (1H, dd, $J_{4,3}$ 7.6, $J_{4,5}$ 6.3, $J_{4,5'}$ 2.0, H-4), 4.80 (1H, dd, $J_{5',5}$ 12.4, $J_{5',4}$ 2.0, H-5'); $^{13}$C NMR $\delta_C$ (100 MHz, CD$_3$CN): 17.18 (d, $^2J_{C,F}$ 24.5, CH$_3$), 66.56 (C-5), 72.43 (d, $^2J_{C,F}$ 16.9, C-3), 79.61 (C-4), 92.98 (d, $^1J_{C,F}$ 179.5, C-2), 171.00 (d, $^2J_{C,F}$ 21.5, C=O); $^{19}$F NMR $\delta_F$ (376 MHz, CD$_3$CN): −169.28 (1F, m, $^3J_{F,H}$ 22.9, F). NMR assignments confirmed using COSY, HMQC, HMBC and nOe experiments; Mass Spec m/z (APCI-): 163.2 ([M−H]$^-$, 30%), 143.2 (100%).

[1] Possible contamination with residual TFA.

Example 4

2-Deoxy-2-fluoro-2-C-methyl-D-ribono-1,4-lactone

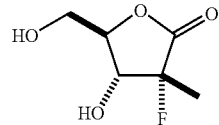

2-Deoxy-2-fluoro-3,4-O-isopropylidene-2-C-methyl-D-ribono-1,5-lactone (1.29 g, 6.317 mmol) was dissolved in anhydrous 1,4-dioxane (36.7 ml) under an atmosphere of argon. A pre-mixed solution of trifluoroacetic acid (146.8 ml) in water (36.7 ml) was added to the mixture slowly at room temperature. After 48 h, t.l.c. (ethyl acetate/heptane, 3:1) indicated conversion of the starting material ($R_f$ 0.57) to faint products ($R_f$ 0.47, 0.43, 0.38). The solvents were removed in vacuo at 35° C. and then coevaporated with toluene (5 ml×2). The crude off-white/brown residue (1.27 g) was purified by flash column chromatography (pre-adsorbed onto silica from ethyl acetate, eluted with ethyl acetate/heptane, 2:1) to give 2-deoxy-2-fluoro-2-C-methyl-D-ribono-1,4-lactone (862 mg, 83%, eluted second) as a white solid and 2-deoxy-2-fluoro-2-C-methyl-D-ribono-1,5-lactone (61 mg, 6%, eluted first) as a white solid, along with mixed fractions (115 mg, 11%).

Data for 2-deoxy-2-fluoro-2-C-dimethyl-D-ribono-1,4-lactone $C_6H_9FO_4$ 164.13 gmol$^{-1}$; $R_f$=0.45, ethyl acetate/heptane, 8:1; m.p.: 142-143° C.; $[\alpha]_D^{20}$: +129.323 (c, 0.9138 in CH$_3$CN); $\nu_{max}$ (KBr disc): 3412 cm$^{-1}$, 3274 cm$^{-1}$ (O—H), 1777 cm$^{-1}$ (C=O); $^1$H NMR $\delta_H$ (400 MHz, CD$_3$CN): 1.55 (3H, d, $J_{H,F}$ 23.5, CH$_3$), 2.22 (1H, br-s, OH), 3.17 (1H, br-s, OH), 3.69 (1H, dd, $J_{5,5'}$ 13.3, $J_{5,4}$ 3.7, H-5), 3.92 (1H, dd, $J_{5',5}$ 13.3, $J_{5',4}$ 1.5, H-5'), 4.05 (1H, dd, $^3J_{H,F}$ 21.5, $J_{3,4}$ 7.2, H-3), 4.32 (1H, m, H-4); $^{13}C$ NMR $\delta_C$ (100 MHz, CD$_3$CN): 17.63 (d, $^2J_{C,F}$ 25.3, CH$_3$), 60.19 (C-5), 71.85 (d, $^2J_{C,F}$ 16.9, C-3), 83.94 (C-4), 94.55 (d, $^1J_{C,F}$ 178.7, C-2), 172.04 (d, $^2J_{C,F}$ 21.5, C=O); $^{19}F$ NMR $\delta_F$ (376 MHz, CD$_3$CN): −168.69 (1F, m, $^3J_{F,H}$ 23.3, F). NMR assignments confirmed using COSY, HMQC, HMBC and nOe experiments; Mass Spec m/z (APCI-): 163.2 ([M−H]$^-$, 40%), 143.2 (100%). Microanalysis: C$_6$H$_9$FO$_4$ calculated C, 43.91%, H, 5.53%, found C, 44.18%, H, 5.73%. Crystals grown from ethyl acetate/hexane.

Example 5

3,5-Di-benzoyl-2-deoxy-2-fluoro-2-C-methyl-D-ribono-1,4-lactone

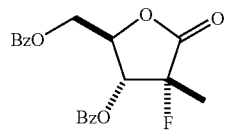

2-Deoxy-2-fluoro-2-C-methyl-D-ribono-1,4-lactone (200 mg, 1.219 mmol) was dissolved in anhydrous pyridine (2.4 ml) and cooled to 0° C. under an atmosphere of argon. Benzoyl chloride (353 µl, 3.05 mmol) was added dropwise over 5 min. The solution was allowed to warm to room temperature and stirred for 4 h. Benzoyl chloride (142 µl, 1.219 mmol) was added dropwise and the mixture was stirred for 16 h after which time a further portion of benzoyl chloride (142 µl, 1.219 mmol) was added. Having stirred the solution for a further 3 h, a final portion of benzoyl chloride (142 µl, 1.219 mmol) was added and left for a further 1 h. T.l.c. (ethyl acetate/heptane, 2:3) indicated complete conversion of the starting material (R$_f$ 0.16) to faintly stained, but UV active products (R$_f$ 0.67, 0.63). The reaction was quenched with water (1 ml) and the solids dissolved. After stirring at room temperature for 5 min crystals precipitated from the solution which were filtered and washed with water (2 ml×2) and found by t.l.c. to contain two UV active components and pyridine. The dried, sticky solid (400 mg) was therefore dissolved in dichloromethane (10 ml) and subjected to a 1M HCl$_{aq}$ (4 ml×2) wash. The organic layer was dried (magnesium sulfate), filtered and concentrated in vacuo. The crude off-white residue (340 mg) was purified by flash column chromatography (pre-adsorbed onto silica from dichloromethane, eluted with ethyl acetate/heptane, 1:4) to give 3,5-di-benzoyl-2-deoxy-2-fluoro-2-C-methyl-D-ribono-1,4-lactone (272 mg, 60%) as fine, white needles.

Data for 3,5-di-benzoyl-2-deoxy-2-fluoro-2-C-methyl-D-ribono-1,4-lactone C$_{20}$H$_{17}$FO$_6$ 372.34 gmol$^{-1}$; R$_f$=0.62, ethyl acetate/heptane, 2:3; m.p.: 123-125° C.; $[\alpha]_D^{20}$: +102.943 (c, 0.8728 in CH$_3$CN); $\nu_{max}$ (thin film): 1793 cm$^{-1}$ (C=O, α-fluoro-γ-lactone), 1733 cm$^{-1}$, 1717 cm$^{-1}$ (C=O, Bz); $^1H$ NMR $\delta_H$ (400 MHz, CD$_3$CN): 1.74 (3H, d, $J_{H,F}$ 24.1, CH$_3$), 4.62 (1H, dd, $J_{5,5'}$ 12.7, $J_{5,4}$ 5.6, H-5), 4.75 (1H, dd, $J_{5',5}$ 12.7, $J_{5',4}$ 3.5, H-5'), 5.07 (1H, ddd, $J_{4,3}$ 7.2, $J_{4,5}$ 5.6, $J_{4,5'}$ 3.5, H-4), 5.62 (1H, dd, $^3J_{H,F}$ 17.7, $J_{3,4}$ 7.2, H-3); 7.48, 7.55 (4H, 2×t, 4×H$_{meta}$), 7.64, 7.70 (2H, 2×t, 2×H$_{para}$), 8.01, 8.09 (4H, 2×t, 4×H$_{ortho}$); $^{13}C$ NMR $\delta_C$ (100 MHz, CD$_3$CN): 18.88 (d, $^2J_{C,F}$ 24.5, CH$_3$), 63.51 (C-5), 73.07 (d, $^2J_{C,F}$ 14.6, C-3), 78.84 (C-4), 92.61 (d, $^1J_{C,F}$ 185.6, C-2), 129.51, 130.53 (2×C$_{ipso}$), 129.64, 129.78 (2×C$_{meta}$), 130.43, 130.76 (2×C$_{ortho}$), 134.46, 135.00 (2×C$_{para}$), 166.22, 166.63 (2×CO$_2$Bz), 170.64 (d, $^2J_{C,F}$ 21.0, C=O); $^{19}F$ NMR $\delta_F$ (376 MHz, CD$_3$CN): −164.77 (1F, m, $^3J_{F,H}$ 24.4, F). NMR assignments confirmed using COSY, HMQC, HMBC and nOe experiments; Mass Spec m/z (ESI-): 373.1 ([M+H]$^+$, 50%), 390.2 ([M+NH$_4$]$^+$, 100%); HPLC (272 nm) R$_t$=6.17 (98%); Microanalysis: C$_{20}$H$_{17}$FO$_6$ calculated C, 64.51%, H, 4.60%, found C, 64.56%, H, 4.66%.

The foregoing merely is illustrative of the invention and is not intended to limit the invention to the disclosed processes and reaction conditions. Variations that are obvious to one of ordinary skill in the art are intended to be included within the spirit and scope of the invention as defined in the appended claims

What is claimed is:

1. A process of preparing a compound of Formula II

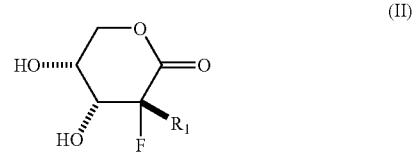

wherein R$^1$ is straight chained, or branched alkyl, cycloalkyl, alkenyl, alkynyl, alkenyl, CF$_3$, cyano, aryl, aralkyl, or heterocycle comprising:

a) providing a compound of structure (i) or (ii)

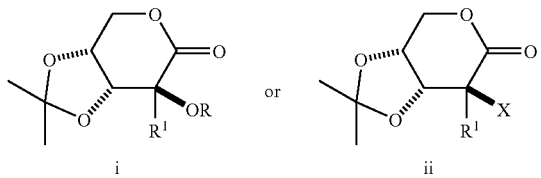

where OR is a leaving group and X is halogen;
b) contacting the compound with a fluorinating agent under anhydrous conditions; and
c) removing the hydroxyl protecting ketal group from the product of step b).

2. The process of claim 1 wherein the fluorinating agent is tris(dimethylamino)sulfonium difluorotrimethyl silicate (TASF).

3. The process of claim 1 wherein a compound of Formula (II) is produced in at least 40% or more yields.

4. The process of claim 1 wherein R' is methyl.

5. The process of claim 1 wherein R$^1$ is ethyl.

6. The process of claim 1 wherein R$^1$ is vinyl.

7. The process of claim 1 wherein R$^1$ is —C≡CH.

8. The process of claim 1 wherein OR is selected from the group consisting of triflate, mesylate, and tosylate.

9. The process of claim 1 wherein X in Formula (II) is bromine, chlorine or iodine.

10. The process of claim 8 wherein OR is triflate.

11. The process of claim 1 wherein the reaction contains less than 1% water.

12. The process of claim 1 wherein the reaction contains less than 0.1% water.

13. The process of claim 1 wherein the reaction contains less than 0.01% water.

14. The process of claim 1 further comprising converting a compound of Formula (II) to a 1,4-lactone compound by contacting the product from step (b) with an organic acid in an organic solvent.

15. The process of claim 14 wherein the acid is trifluoroacetic acid.

16. The process of claim 14 wherein the acid is an aryl or alkyl sulfonic acid.

17. The process of claim 16 wherein the acid is methanesulfonic acid.

18. The process of claim 16 wherein the acid is p-toluenesulfonic acid.

19. The process of claim 14 wherein the solvent is 1,4-dioxane.

20. The process of claim 14 wherein 1,4-lactone compound is a compound of Formula (B)

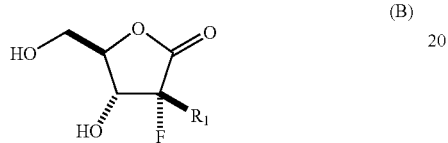

(B)

wherein $R^1$ is $C_{1-4}$ lower alkyl, alkenyl, alkynyl or $CF_3$.

21. The process of claim 14 wherein the 1,4-lactone compound is a 2-deoxy-2-fluoro-2-C-methyl-D-ribono-1,4-lactone.

22. The process of claim 20 wherein $R^1$ is acetylene.

23. The process of claim 20 wherein $R^1$ is vinyl.

24. The process of claim 14 further comprising:
d) reducing the 1,5-lactone product of step c) to a hemiacetal, e) derivatizing the hydroxyl from step d) to a suitable leaving group; and f) contacting the product of step e) with a purine or pyrimidine base to provide a 2'-branched nucleoside compound.

25. The process of claim 1, wherein the compound of Formula (i) is 3,4-O-isopropylidene-2-C-methyl-2-O-trifluoromethanesulfonyl-D-arabinono-1,5-lactone.

26. The process of claim 1 wherein a 2-deoxy-2-fluoro-3,4-O-isopropylidene-2-C-methyl-D-ribono-1,5-lactone is produced.

27. The process of claim 1 wherein step (b) is carried out at a temperature below 0° C.

28. The process of claim 1 wherein step (b) is carried out at a temperature below −5° C.

29. A process for preparing a 2-deoxy-2-alkyl-2-halo-lactone compound comprising:

a) reacting the 2-position of an isopropylidene, 2-alkyl-substituted arabinono-1,5-lactone compound with a leaving group reagent, to provide a 2-deoxy-2-alkyl-substituted-3,4-isopropylidene arabinono-1,5-lactone substituted with a leaving group at the 2-position selected from the group consisting of p-toluene sulfonate, methanesulfonate, trifluoromethanesulfonate, allylsulfonate, 4-nitrobenzenesulfonate, 4-bromobenzenesulfonate, acetate, trifluoroacetate, arylsulfate and alkylsulfonate;

b) reacting the product from step a) with a fluorinating agent, a chlorinating agent, a brominating agent or an iodinating reagent to provide a 2-deoxy-2-halo-2-alkyl-substituted-3,4-isopropylidene ribono-1,5-lactone;

c) deprotecting the product from step b) with an acid to provide a 2-deoxy-2-halo-2-alkyl-substituted ribono-1,4-lactone as a major product and a 2-deoxy-2-halo-2-alkyl-substituted ribono-1,5-lactone as a minor product; and d) optionally protecting one or more hydroxy groups on either one of the products from step c.

30. The process of claim 29, step a) wherein the 2-deoxy-2-alkyl-substituted isopropylidene arabinono-1,5-lactone substituted with a leaving group at the 2-position is 3,4-O-isopropylidene-2-C-methyl-2-O-trifluoromethanesulfonyl-D-arabinono-1,5-lactone.

31. The process of claim 29, step b) wherein the 2-deoxy-2-halo-2-alkyl-substituted-3,4-isopropylidene ribono-1,5-lactone is 2-deoxy-2-fluoro-3,4-O-isopropylidene-2-C-methyl-D-ribono-1,5-lactone.

32. The process of claim 29, step c) wherein the 2-deoxy-2-halo-2-alkyl-substituted ribono-1,4-lactone major product is 2-deoxy-2-fluoro-2-C-methyl-D-ribono-1,4-lactone.

33. The process of claim 29, step c) wherein the 2-deoxy-2-halo-2-alkyl-substituted ribono-1,4-lactone minor product is 2-deoxy-2-fluoro-2-C-methyl-D-ribono-1,5-lactone.

34. The process of claim 29, step d) wherein benzoyl is the protecting group on one or more hydroxy groups on either of one of the products from claim 1, step c).

35. The process of claim 29 wherein the fluorinating agent is TASF.

36. The process of claim 29, step c) wherein the deprotecting reagent is trifluoroacetic acid (TFA).

37. The process of claim 29, step a) wherein the leaving group is selected from the group consisting of triflate, mesylate.

38. The process of claim 37 wherein the leaving group is triflate.

* * * * *